(12) United States Patent
Campbell et al.

(10) Patent No.: US 9,463,004 B2
(45) Date of Patent: Oct. 11, 2016

(54) BIOMATERIALS FOR TRACK AND PUNCTURE CLOSURE

(75) Inventors: Patrick Campbell, Wayland, MA (US); Amarpreet S. Sawhney, Lexington, MA (US)

(73) Assignee: Incept, LLC., Lexington, MA (US)

( * ) Notice: Subject to any disclaimer, the term of this patent is extended or adjusted under 35 U.S.C. 154(b) by 382 days.

(21) Appl. No.: 12/773,326

(22) Filed: May 4, 2010

(65) Prior Publication Data
US 2010/0280546 A1  Nov. 4, 2010

Related U.S. Application Data

(60) Provisional application No. 61/175,220, filed on May 4, 2009, provisional application No. 61/265,977, filed on Dec. 2, 2009.

(51) Int. Cl.
*A61B 17/03* (2006.01)
*A61B 17/00* (2006.01)

(52) U.S. Cl.
CPC .. *A61B 17/0057* (2013.01); *A61B 2017/00004* (2013.01); *A61B 2017/0065* (2013.01); *A61B 2017/00654* (2013.01)

(58) Field of Classification Search
CPC .............. A61B 17/0057; A61B 2017/0065; A61B 2017/00654; A61B 2017/00676; A61B 2017/00646; A61B 2017/00623; A61B 2017/00601
USPC ........................................................ 606/213
See application file for complete search history.

(56) References Cited

U.S. PATENT DOCUMENTS

| | | |
|---|---|---|
| 2,115,492 A | 4/1938 | Kober |
| 3,765,419 A | 10/1973 | Usher |
| 4,002,173 A | 1/1977 | Manning |
| 4,260,077 A | 4/1981 | Schroeder |
| 4,327,709 A | 5/1982 | Hanson et al. |
| 4,362,150 A | 12/1982 | Lombardi, Jr. et al. |
| 4,472,542 A | 9/1984 | Nambu |
| 4,540,404 A | 9/1985 | Wolvek |
| 4,655,211 A | 4/1987 | Sakamoto et al. |
| 4,664,857 A | 5/1987 | Nambu |
| 4,734,097 A | 3/1988 | Tanabe et al. |
| 4,738,658 A | 4/1988 | Magro et al. |
| 4,826,945 A | 5/1989 | Cohn et al. |
| 4,838,280 A | 6/1989 | Haaga |

(Continued)

FOREIGN PATENT DOCUMENTS

| | | |
|---|---|---|
| EP | 0476178 | 3/1992 |
| EP | 0482350 | 4/1992 |

(Continued)

OTHER PUBLICATIONS

Gander et al., "Crosslinked Poly(alkylene Oxides) for the Preparation of Controlled Release Micromatrices", Journal of Controlled Release, 5:271-283 (1988).

(Continued)

*Primary Examiner* — Julian W Woo
*Assistant Examiner* — Shaun L David
(74) *Attorney, Agent, or Firm* — Dardi & Herbert, PLLC; Curtis B. Herbert

(57) ABSTRACT

Embodiments include coatings for adherence of biomaterials to a tissue. Systems and methods for adapting such coated materials to vascular access closure are further proved.

28 Claims, 25 Drawing Sheets

(56) References Cited

U.S. PATENT DOCUMENTS

| | | |
|---|---|---|
| 4,852,568 A | 8/1989 | Kensey |
| 4,890,612 A | 1/1990 | Kensey |
| 4,938,763 A | 7/1990 | Dunn et al. |
| 5,061,274 A | 10/1991 | Kensey |
| 5,104,375 A | 4/1992 | Wolf et al. |
| 5,104,389 A | 4/1992 | Deem et al. |
| 5,108,421 A | 4/1992 | Fowler |
| 5,192,300 A | 3/1993 | Fowler |
| 5,192,302 A | 3/1993 | Kensey et al. |
| 5,221,259 A | 6/1993 | Weldom et al. |
| 5,222,974 A | 6/1993 | Kensey et al. |
| 5,258,042 A | 11/1993 | Mehta |
| 5,259,835 A | 11/1993 | Clark et al. |
| 5,275,616 A | 1/1994 | Fowler |
| 5,290,310 A | 3/1994 | Makower et al. |
| 5,292,332 A | 3/1994 | Lee |
| 5,306,254 A | 4/1994 | Nash et al. |
| 5,320,639 A | 6/1994 | Rudnick |
| 5,324,306 A | 6/1994 | Makower et al. |
| 5,334,216 A | 8/1994 | Vidal |
| 5,376,375 A | 12/1994 | Rhee et al. |
| 5,383,896 A | 1/1995 | Gershony |
| RE34,866 E | 2/1995 | Kensey et al. |
| 5,391,183 A | 2/1995 | Janzen et al. |
| 5,409,703 A | 4/1995 | McAnalley et al. |
| 5,410,016 A | 4/1995 | Hubbell et al. |
| 5,413,571 A | 5/1995 | Katsaros et al. |
| 5,419,765 A | 5/1995 | Weldon et al. |
| 5,431,639 A | 7/1995 | Shaw |
| 5,437,292 A | 8/1995 | Kipshidze et al. |
| 5,437,631 A | 8/1995 | Janzen |
| 5,441,517 A | 8/1995 | Kensey et al. |
| 5,443,481 A | 8/1995 | Lee |
| 5,456,693 A | 10/1995 | Conston et al. |
| 5,462,990 A | 10/1995 | Hubbell et al. |
| 5,464,396 A | 11/1995 | Barta et al. |
| 5,486,195 A | 1/1996 | Myers et al. |
| 5,489,278 A | 2/1996 | Abrahamson |
| 5,510,418 A | 4/1996 | Rhee et al. |
| 5,514,158 A | 5/1996 | Kanesaka |
| 5,514,379 A | 5/1996 | Weissleder et al. |
| 5,529,577 A | 6/1996 | Hammerslag |
| 5,541,234 A | 7/1996 | Unger et al. |
| 5,550,187 A | 8/1996 | Rhee et al. |
| 5,571,181 A | 11/1996 | Li |
| 5,580,923 A | 12/1996 | Yeung et al. |
| 5,583,114 A | 12/1996 | Barrows et al. |
| 5,591,204 A | 1/1997 | Janzen et al. |
| 5,591,205 A | 1/1997 | Fowler |
| 5,601,602 A | 2/1997 | Fowler |
| 5,626,601 A | 5/1997 | Gershony et al. |
| 5,627,233 A | 5/1997 | Hubbell et al. |
| 5,643,464 A | 7/1997 | Rhee et al. |
| 5,660,849 A | 8/1997 | Polson et al. |
| 5,672,662 A | 9/1997 | Harris et al. |
| 5,700,477 A | 12/1997 | Rosenthal et al. |
| 5,714,159 A | 2/1998 | Shalaby |
| 5,716,375 A | 2/1998 | Fowler |
| 5,718,916 A | 2/1998 | Scherr |
| 5,725,498 A | 3/1998 | Janzen |
| 5,725,551 A | 3/1998 | Myers et al. |
| 5,728,122 A | 3/1998 | Leschinsky et al. |
| 5,731,368 A | 3/1998 | Stanley et al. |
| 5,741,223 A | 4/1998 | Janzen et al. |
| 5,744,153 A | 4/1998 | Yewey et al. |
| 5,744,545 A | 4/1998 | Rhee et al. |
| 5,752,974 A | 5/1998 | Rhee et al. |
| 5,780,044 A | 7/1998 | Yewey et al. |
| 5,782,860 A | 7/1998 | Epstein et al. |
| 5,785,679 A | 7/1998 | Abolfthi et al. |
| 5,795,331 A | 8/1998 | Cragg et al. |
| 5,826,584 A | 10/1998 | Schmitt |
| 5,830,130 A | 11/1998 | Janzen et al. |
| 5,836,970 A | 11/1998 | Pandit |
| 5,843,124 A | 12/1998 | Hammerslag |
| 5,843,743 A | 12/1998 | Hubbell et al. |
| 5,849,412 A | 12/1998 | Bromberg et al. |
| 5,874,500 A | 2/1999 | Rhee et al. |
| 5,916,236 A | 6/1999 | Muijs Van de Moer et al. |
| 5,932,462 A | 8/1999 | Harris et al. |
| 5,948,429 A | 9/1999 | Bell et al. |
| 5,948,829 A | 9/1999 | Wallajapet et al. |
| 5,955,549 A | 9/1999 | Chang et al. |
| 5,972,375 A | 10/1999 | Truter et al. |
| 5,973,014 A | 10/1999 | Funk et al. |
| 6,017,359 A | 1/2000 | Gershony |
| 6,022,361 A | 2/2000 | Epstein et al. |
| 6,027,471 A | 2/2000 | Fallon et al. |
| 6,045,570 A | 4/2000 | Epstein et al. |
| 6,048,358 A | 4/2000 | Barak |
| 6,051,248 A | 4/2000 | Sawhney et al. |
| 6,056,768 A | 5/2000 | Cates et al. |
| 6,056,769 A | 5/2000 | Epstein et al. |
| 6,063,061 A | 5/2000 | Wallace et al. |
| 6,083,522 A | 7/2000 | Chu |
| 6,093,388 A | 7/2000 | Ferguson |
| 6,100,346 A | 8/2000 | Jamiolkowski et al. |
| 6,129,761 A | 10/2000 | Hubbell |
| 6,133,325 A | 10/2000 | Schwartz et al. |
| 6,149,931 A | 11/2000 | Schwartz et al. |
| 6,152,943 A | 11/2000 | Sawhney |
| 6,162,240 A | 12/2000 | Cates et al. |
| 6,162,241 A | 12/2000 | Coury et al. |
| 6,165,201 A | 12/2000 | Sawhney |
| 6,166,130 A | 12/2000 | Rhee et al. |
| 6,179,862 B1 | 1/2001 | Sawhney |
| 6,238,412 B1 | 5/2001 | Dubrul et al. |
| 6,251,382 B1 | 6/2001 | Greenwald et al. |
| 6,258,351 B1 | 7/2001 | Harris |
| 6,261,544 B1 | 7/2001 | Coury et al. |
| 6,271,278 B1 | 8/2001 | Park et al. |
| 6,287,323 B1 | 9/2001 | Hammerslag |
| 6,296,658 B1 | 10/2001 | Gershony |
| 6,299,597 B1 | 10/2001 | Buscemi et al. |
| 6,302,898 B1 | 10/2001 | Edwards et al. |
| 6,312,725 B1 | 11/2001 | Wallace et al. |
| 6,350,274 B1 | 2/2002 | Li |
| 6,368,300 B1 | 4/2002 | Fallon et al. |
| 6,371,975 B2 | 4/2002 | Cruise et al. |
| 6,379,373 B1 | 4/2002 | Sawhney et al. |
| 6,458,147 B1 | 10/2002 | Cruise et al. |
| 6,458,156 B1 | 10/2002 | Wan et al. |
| 6,458,889 B1 | 10/2002 | Trollsas et al. |
| 6,475,177 B1 | 11/2002 | Suzuki |
| 6,495,127 B1 | 12/2002 | Wallace et al. |
| 6,514,534 B1 | 2/2003 | Sawhney |
| 6,517,824 B1 | 2/2003 | Kohn et al. |
| 6,544,276 B1 | 4/2003 | Azizi |
| 6,562,059 B2 | 5/2003 | Edwards et al. |
| 6,566,406 B1 | 5/2003 | Pathak et al. |
| 6,569,185 B2 | 5/2003 | Ungs |
| 6,592,614 B2 | 7/2003 | Lenker et al. |
| 6,599,515 B1 | 7/2003 | Delmotte |
| 6,605,294 B2 | 8/2003 | Sawhney |
| 6,608,117 B1 | 8/2003 | Gvozdic |
| 6,610,033 B1 | 8/2003 | Melanson et al. |
| 6,613,070 B2 | 9/2003 | Redmond et al. |
| 6,632,457 B1 | 10/2003 | Sawhney |
| 6,635,068 B1 | 10/2003 | Dubrul et al. |
| 6,639,014 B2 | 10/2003 | Pathak et al. |
| 6,673,093 B1 | 1/2004 | Sawhney |
| 6,689,148 B2 | 2/2004 | Sawhney |
| 6,699,261 B1 | 3/2004 | Cates et al. |
| 6,703,047 B2 | 3/2004 | Sawhney et al. |
| 6,774,151 B2 | 8/2004 | Malmgren et al. |
| 6,818,008 B1 | 11/2004 | Cates |
| 6,818,018 B1 | 11/2004 | Sawhney |
| 6,833,408 B2 | 12/2004 | Sehl et al. |
| 6,863,924 B2 | 3/2005 | Ranganathan et al. |
| 6,887,974 B2 | 5/2005 | Pathak |
| 6,890,342 B2 | 5/2005 | Zhu et al. |
| 6,893,431 B2 | 5/2005 | Naimark et al. |
| 6,916,857 B2 | 7/2005 | Won et al. |
| 6,923,986 B2 | 8/2005 | Pathak et al. |

(56) References Cited

U.S. PATENT DOCUMENTS

| | | |
|---|---|---|
| 6,958,212 B1 | 10/2005 | Hubbell et al. |
| 6,960,617 B2 | 11/2005 | Omidian et al. |
| 6,962,979 B1 | 11/2005 | Rhee |
| 7,001,410 B2 | 2/2006 | Fisher |
| 7,153,519 B2 | 12/2006 | Hubbell et al. |
| 7,220,270 B2 | 5/2007 | Sawhney et al. |
| 7,332,566 B2 | 2/2008 | Pathak et al. |
| 7,335,220 B2 | 2/2008 | Khosravi et al. |
| 7,597,882 B2 | 10/2009 | Pathak et al. |
| 7,648,713 B2 | 1/2010 | Sawhney |
| 7,780,980 B2 | 8/2010 | Sawhney |
| 2001/0003158 A1* | 6/2001 | Kensey et al. ............... 606/213 |
| 2001/0031948 A1 | 10/2001 | Cruise et al. |
| 2001/0046518 A1 | 11/2001 | Sawhney |
| 2001/0047187 A1 | 11/2001 | Milo et al. |
| 2001/0051813 A1 | 12/2001 | Hnojewyj |
| 2002/0015724 A1 | 2/2002 | Yang et al. |
| 2002/0062104 A1 | 5/2002 | Ashby et al. |
| 2002/0072767 A1 | 6/2002 | Zhu |
| 2002/0106409 A1 | 8/2002 | Sawhney et al. |
| 2002/0111392 A1 | 8/2002 | Cruise |
| 2002/0111651 A1 | 8/2002 | Ungs |
| 2002/0120228 A1 | 8/2002 | Maa et al. |
| 2002/0188319 A1 | 12/2002 | Morris et al. |
| 2003/0008831 A1 | 1/2003 | Yang et al. |
| 2003/0012734 A1 | 1/2003 | Pathak et al. |
| 2003/0014075 A1 | 1/2003 | Rosenbluth et al. |
| 2003/0051735 A1 | 3/2003 | Pavcnik et al. |
| 2003/0088269 A1 | 5/2003 | Ashby |
| 2003/0088271 A1 | 5/2003 | Cragg et al. |
| 2003/0100921 A1 | 5/2003 | Addis et al. |
| 2003/0135234 A1 | 7/2003 | Fisher et al. |
| 2003/0135236 A1 | 7/2003 | Fisher et al. |
| 2003/0139770 A1 | 7/2003 | Fisher et al. |
| 2003/0139771 A1 | 7/2003 | Fisher et al. |
| 2003/0139772 A1 | 7/2003 | Fisher et al. |
| 2003/0139773 A1 | 7/2003 | Fisher et al. |
| 2003/0233120 A1 | 12/2003 | Akerfeidt |
| 2004/0063206 A1 | 4/2004 | Rowley et al. |
| 2004/0093015 A1 | 5/2004 | Ogle |
| 2004/0121905 A1 | 6/2004 | Ranganathan et al. |
| 2004/0122350 A1 | 6/2004 | Zhong et al. |
| 2004/0137067 A1 | 7/2004 | Narang et al. |
| 2004/0147016 A1 | 7/2004 | Rowley et al. |
| 2004/0249342 A1 | 12/2004 | Khosravi et al. |
| 2004/0267308 A1 | 12/2004 | Bagaoisan et al. |
| 2005/0169882 A1 | 8/2005 | Lowe et al. |
| 2006/0034930 A1 | 2/2006 | Khosravi et al. |
| 2006/0047313 A1 | 3/2006 | Khanna et al. |
| 2006/0079599 A1 | 4/2006 | Arthur |
| 2006/0088567 A1* | 4/2006 | Warner et al. ............... 424/422 |
| 2006/0099238 A1 | 5/2006 | Khosravi et al. |
| 2006/0100664 A1 | 5/2006 | Pai et al. |
| 2007/0060950 A1* | 3/2007 | Khosravi et al. ............ 606/213 |
| 2007/0231366 A1 | 10/2007 | Sawhney et al. |
| 2008/0077178 A1 | 3/2008 | Janzen et al. |
| 2008/0220047 A1 | 9/2008 | Sawhney et al. |
| 2009/0017097 A1 | 1/2009 | Sawhney et al. |
| 2009/0215923 A1 | 8/2009 | Carnahan et al. |

FOREIGN PATENT DOCUMENTS

| | | |
|---|---|---|
| EP | 0 732 109 A1 | 9/1996 |
| EP | 1 704 878 A2 | 9/2006 |
| EP | 1 967 220 A2 | 9/2008 |
| WO | 9222252 | 12/1992 |
| WO | 9413210 | 6/1994 |
| WO | 97/05185 A2 | 2/1997 |
| WO | 97/22371 A1 | 6/1997 |
| WO | 97/39781 A1 | 10/1997 |
| WO | 98/12274 A1 | 3/1998 |
| WO | 98/35631 A1 | 8/1998 |
| WO | 98/03454 A1 | 1/1999 |
| WO | 99/03454 A1 | 1/1999 |
| WO | 99/08718 A3 | 2/1999 |
| WO | 99/22770 A1 | 5/1999 |
| WO | 9922646 | 5/1999 |
| WO | 99/34833 A1 | 7/1999 |
| WO | 00/09190 A1 | 2/2000 |
| WO | 00/12018 A1 | 3/2000 |
| WO | 00/14155 A1 | 3/2000 |
| WO | 00/19912 A1 | 4/2000 |
| WO | 01/66038 A2 | 9/2001 |
| WO | 03009764 | 2/2003 |
| WO | 03087254 | 10/2003 |
| WO | 03094749 | 11/2003 |
| WO | 2004/028404 A2 | 4/2004 |
| WO | 2006/026325 A2 | 3/2006 |
| WO | 2006/031388 A2 | 3/2006 |
| WO | 2007/001926 A2 | 1/2007 |
| WO | 2007/005249 A2 | 1/2007 |
| WO | 2007067621 | 6/2007 |

OTHER PUBLICATIONS

Sawhney et al., "Bioerodible Hydrogels Based on Photopolymerized Poly(ethylene glycol)co-poly(α-hydroxy acid) Diacrylate Macromers," Macromolecules, 26:581-587 (1993).

Sawhney et al., "Optimization of Photopolymerized Bioerodible Hydrogel Properties for Adhesion Prevention", Journal of Biomedical Materials Research, 28:831-838 (1994).

International Search Report (PCT/US2010/033488) dated Mar. 24, 2011.

Supplementary European Search Report from Corresponding Application EP10772669 dated Feb. 6, 2014, 9 pages.

* cited by examiner

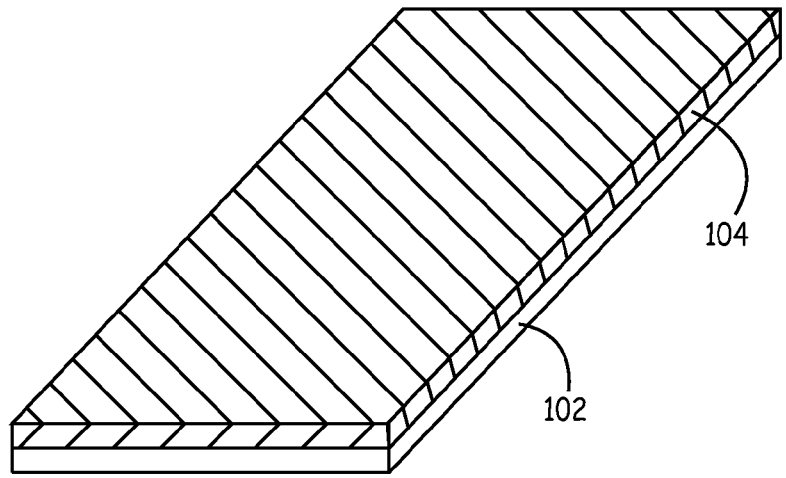
FIG. 1A
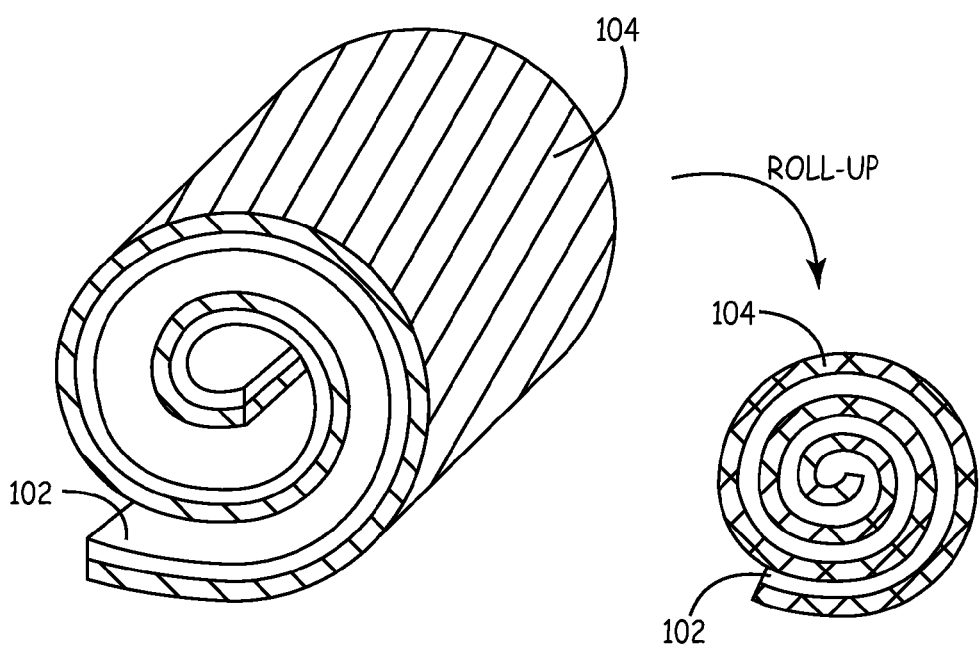
FIG. 1B
FIG. 1C

ROLL

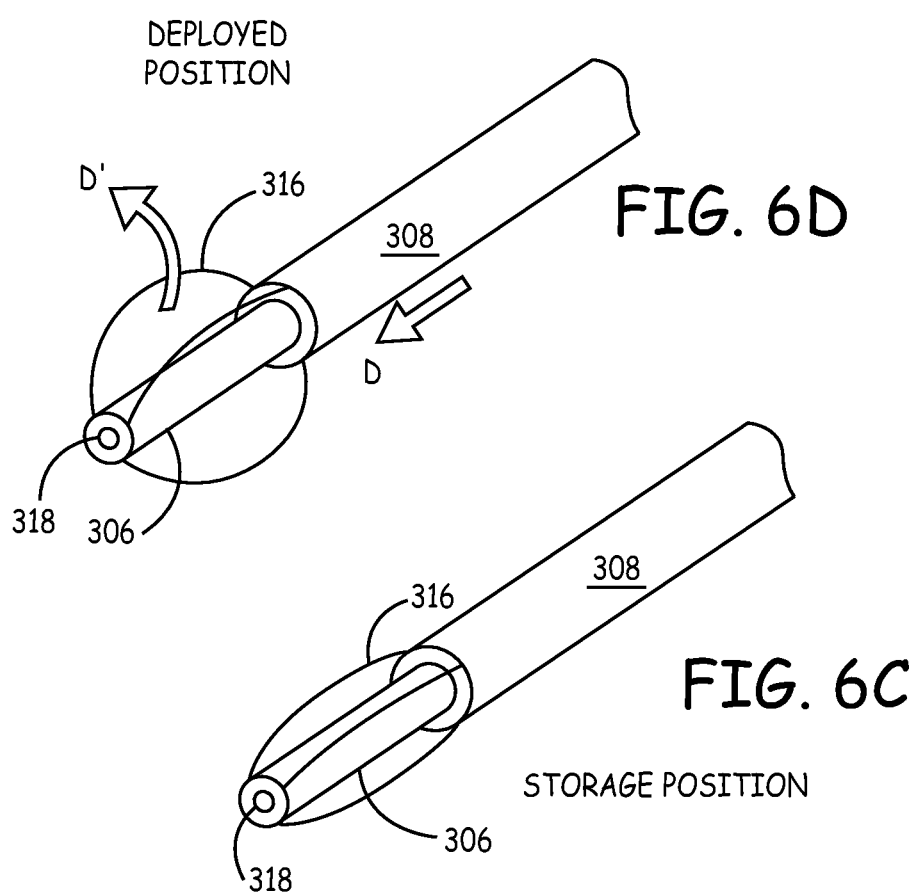

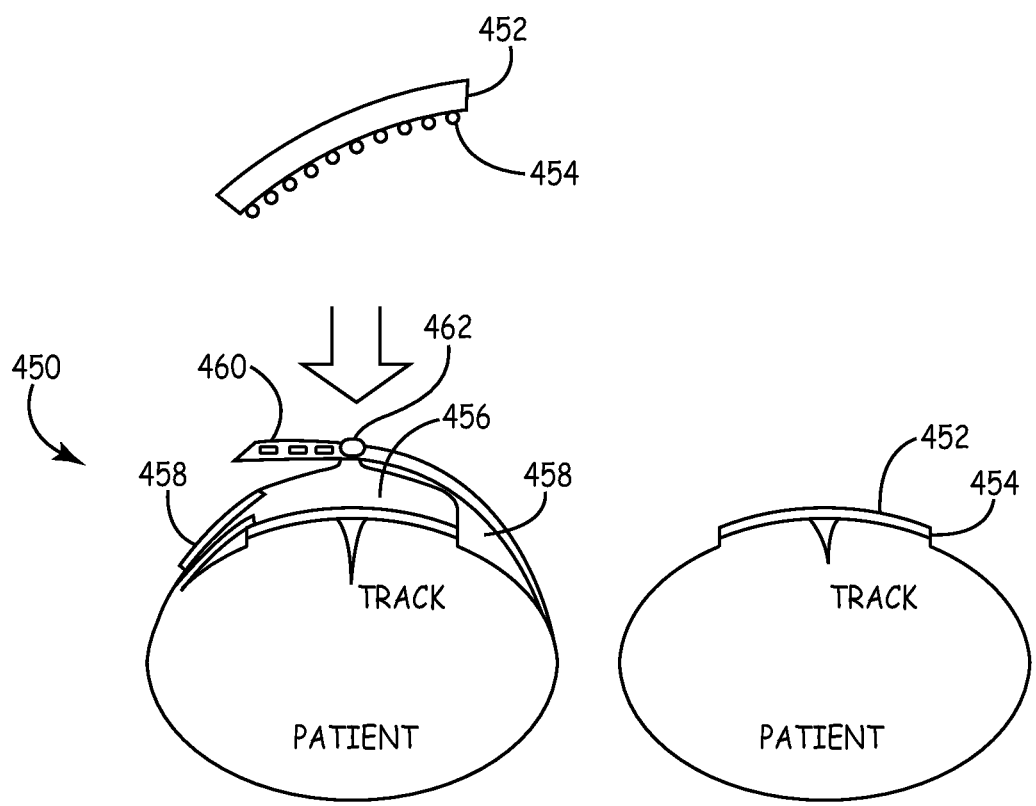

BIOMATERIALS FOR TRACK AND PUNCTURE CLOSURE

CROSS REFERENCE TO RELATED APPLICATIONS

This patent application claims priority to U.S. Ser. No. 61/175,220 filed May 4, 2009 and U.S. Ser. No. 61/265,977 filed Dec. 2, 2009, which are hereby incorporated by reference herein for all purposes.

TECHNICAL FIELD

The technical field relates to surgical methods and closure of punctures, for instance, percutaneous closure of femoral access punctures.

BACKGROUND

Clinicians perform many medical procedures by puncturing a blood vessel and introducing a small tube through the blood vessel that is guided to other parts of the body. A common point of entry is the femoral artery. Once the medical procedure is completed, the artery or other blood vessel has to be adequately closed so the patient can leave the operation site, and the puncture needs to heal.

Many devices have been created to facilitate closure after iatropic punctures have been made in the femoral artery. Examples include devices described in U.S. Pat. Nos. 5,108,421 to Fowler, 5,192,302 or 5,222,974 to Kensey, and US Pub 2006/0100664 to Pai. The PERCLOSE system, introduced in 1994, was the first suture-mediated device to be approved by the Food and Drug Administration. PERCLOSE PROGLIDE is the latest generation, introduced in 2004. It offers improvements in the ease of knot delivery and strength and of the suture material. The system is composed of a sheath, a guide, a knot pusher accessory, and a suture trimmer. The ANGIO-SEAL device is made up of three components: a specially designed polymer anchor, an absorbable collagen sponge, and an absorbable self-tightening suture. The sponge is positioned in the puncture track outside the artery wall by a pulley system created by the anchor and suture. The device seals and sandwiches the arteriotomy between the anchor and the collagen plug. The STARCLOSE is a clip-mediated closure device approved by the Food and Drug Administration in 2005. The STARCLOSE introduces a small, circumferential, flexible clip that mechanically binds the surface of the femoral artery together. The clip is made of nitinol, a nickel-titanium alloy with elastic properties that allow it to return to its original shape once released from the device. Its use involves a multi-step deployment process with a specialized application. The clip is left on the outside of the artery. The MYNX is a rolled-up biodegradable polymer sheet that is pushed into the puncture track and allowed to swell. The swelling secures the device and prevents blood flow.

SUMMARY

A percutaneous puncture of a blood vessel involves creating a track through the skin and puncturing a blood vessel. The need to close the blood vessel is widely recognized because patients have traditionally been required to stay for long times with manual compression. Accordingly, devices have been made to shorten this time. There is another aspect to the closure and healing process, however, which is the sealing of the track that leads to the puncture. Blood from the tissue walls of the track can ooze into the track. Conventional approaches involving a plug inside or at the blood vessel do not address blood seepage from the track. Described herein, however, are devices that address both puncture closure and track sealing.

Further, a vascular closure system that can efficiently close large bore punctures will enable advancement and adoption of additional percutaneous medical tools that would benefit from large access sites. Unfortunately, the force of blood pressure that tends to displace a plug in a blood vessel is proportional to the surface area of the plug so that the forces tending to push a plug out of a puncture increase by a power of two as the plug area is increased. Accordingly, many conventional approaches to plugging a small bore puncture do not scale-up to medium and large bore punctures. A medium bore puncture is defined herein as a puncture made with a gauge between, and inclusive of, 11 F to 14 F. A large bore puncture has a gauge of more than 14 F. A small bore puncture has a gauge of less than 11 F. Described herein, however, are devices that provide medium and large bore sealing.

Certain embodiments herein include techniques for sealing punctures with a combination of a biomaterial tamponade-and-adhesive combination. Another embodiment provides application of adhesives to the track lumen. Another system provides a tamponade biomaterial with adhesive coatings to seal against the track lumen so the material can seal both the track and the artery. Other systems described address closure of an access site that is not femoral but is superficial. For instance, in a brachial access site, there is not enough track available to deploy a conventional vascular closure device.

BRIEF DESCRIPTION OF THE FIGURES

FIG. 1A depicts an embodiment of a coated biomaterial;

FIG. 1B depicts the embodiment of FIG. 1A being rolled-up;

FIG. 1C is a cross-section of the embodiment of FIG. 1B after being rolled-up;

FIG. 6C depicts the delivery apparatus of FIGS. 6A and 6B with the biomaterial sheet removed and the radially expanding member in a storage (undeployed) position;

FIG. 6D Depicts the apparatus of FIG. 6C in a deployed (radially expanded) position;

FIG. 9A depicts a coated plug with a backing and a compression device for compressing the plug on skin of a patient;

FIG. 9B depicts the plug of FIG. 9A in place on a patient's skin;

DETAILED DESCRIPTION OF PREFERRED EMBODIMENTS OF THE INVENTION

Figure 2A:
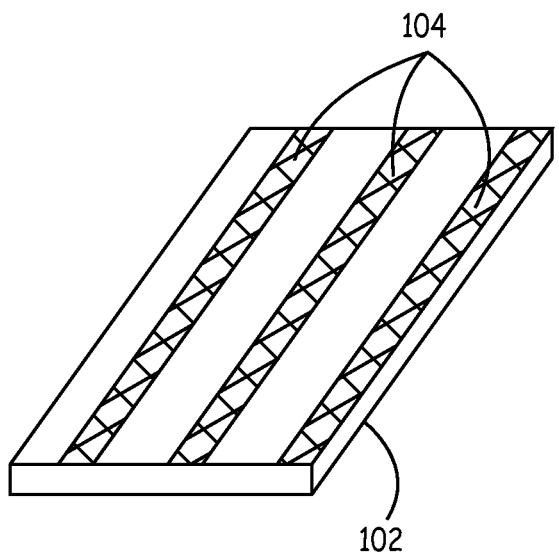
FIG. 2A depicts a partially coated biomaterial with a coating disposed as a plurality of stripes.

An embodiment of the invention is an adhesive plug sized for placement in an iatropic tract. In the case of surgical access procedures, the tract is a track through a tissue that terminates in a blood vessel puncture. The track is a lumen defined by tissue walls. The adhesive plug should be small enough to pass into the track. The plug has a portion that is coated with a precursor or precursors that are substantially dry and react with physiological fluid to dissolve and form a matrix material. The material contributes to forming an adhesive force between the plug and a tissue, which could be walls of the track of tissues at or near the puncture. Coatings enhance closure of the blood vessel and also sealing of the track itself. These and other embodiments create new options for closing large bore or other punctures, for sealing tracks that otherwise tend to ooze blood, and for sealing short tracks. Embodiments described herein include precursors or coated matrices placed into a track, including plugs or sheets.

Coatings and Precursors

FIG. 1A depicts biomaterial sheet 102 with a substantially dry adhesive coating 104 that is non-adherent when substantially dry but is adherent when exposed to a physiological solution (e.g., fluids in a wound or interstitial fluids). The term sheet refers to a generally planar structure with a thickness that is much less than the surface area. The sheet 102 is depicted as rectangular but may have other shapes. FIG. 1B is a conceptual image of how sheet 102 may be rolled-up. FIG. 1C is a cross-sectional view of the same sheet in a fully rolled-up configuration. The sheet may thus be rolled so that it is biased to open by uncurling when unconstrained.

The coatings may be made with precursors that react with each other to create a matrix material. The matrix may be covalently crosslinked, or not, depending on the precursor. Covalently crosslinked materials have a distinct chemical structure from not-covalently crosslinked material, and different properties including mechanical strength and solubility. The matrix may be a hydrogel. A hydrogel is hydrophilic but does not dissolve in water.

Precursors are components that undergo a chemical reaction to become part of a material. Hydrogel precursors can be prepared that react with each other to form covalent bonds in solution, with the precursors forming the structure of the hydrogel and being crosslinked into the hydrogel. In the case of a hydrogel, the dissolution of the precursors accompanied by a natural separation between them in the solution contributes to creating a hydrogel structure. In contrast, a common epoxy or cyanoacrylate material that merely reacts to form a solid is not a hydrogel. Accordingly, some embodiments use a coating made with one or more hydrogel precursors that form a covalently crosslinked hydrogel. The precursors in the coating may be chosen to rapidly dissolve and crosslink upon exposure to physiological fluid. The precursors may be used to prepare coatings that are essentially dry until exposed to a physiological fluid. The fluid drives them into solution so that they can react with each other.

To form covalently crosslinked hydrogels, the precursors must be crosslinked together. In general, polymeric precursors will form polymers that will be joined to other polymers at two or more points, with each point being a linkage to the same or different polymers. Precursors with at least two reactive groups can serve as crosslinkers since each reactive group can participate in the formation of a different growing polymer chain, e.g., as in free radical polymerization. In the case of functional groups without a reactive center, among others, crosslinking requires three or more such functional groups on a precursor. For instance, many electrophilic-nucleophilic reactions consume the electrophilic and nucleophilic functional groups so that a third functional group is needed for the precursor to form a crosslink. Such precursors thus may have three or more functional groups and may be crosslinked by precursors with two or more functional groups. A crosslinked molecule may be crosslinked via an ionic or covalent bond, a physical force, or other attraction. A covalent crosslink, however, will typically offer stability and a chemically distinct structure.

In some embodiments, one or more precursors are multifunctional. Precursors may comprise three or more electrophilic or nucleophilic functional groups, such that a nucleophilic functional group on one precursor may react with an electrophilic functional group on another precursor to form a covalent bond.

The precursors may have biologically inert and hydrophilic portions, e.g., a core. In the case of a branched polymer, a core refers to a contiguous portion of a molecule joined to arms that extend from the core, with the arms having a functional group, which is often at the terminus of the branch. The hydrophilic precursor or precursor portion preferably is water soluble, meaning that it has a solubility of at least 1 g/100 mL in an aqueous solution. A hydrophilic portion may be, for instance, a polyether, for example, polyalkylene oxides such as polyethylene glycol (PEG), polyethylene oxide (PEO), polyethylene oxide-co-polypropylene oxide (PPO), co-polyethylene oxide block or random copolymers, and polyvinyl alcohol (PVA), poly (vinyl pyrrolidinone) (PVP), poly (amino acids, dextran, or a protein). The precursors may have a polyalkylene glycol portion and may be polyethylene glycol based, with at least about 80% or 90% by weight of the polymer comprising polyethylene oxide repeats. The polyethers and more particularly poly (oxyalkylenes) or poly (ethylene glycol) or polyethylene glycol are generally hydrophilic.

A precursor may also be a macromolecule (or macromer), which is a molecule having a molecular weight in the range of a few thousand to many millions. In some embodiments, however, at least one of the precursors is a small molecule of about 1000 Da or less. The macromolecule, when reacted in combination with a small molecule of about 1000 Da or less, is preferably at least five to fifty times greater in molecular weight than the small molecule and is preferably less than about 60,000 Da; artisans will immediately appreciate that all the ranges and values within the explicitly stated ranges are contemplated. A more preferred range is a macromolecule that is about seven to about thirty times greater in molecular weight than the crosslinker and a most preferred range is about ten to twenty times difference in weight. Further, a macromolecular molecular weight of 5,000 to 50,000 is useful, as is a molecular weight of 7,000 to 40,000 or a molecular weight of 10,000 to 20,000; artisans will immediately appreciate that all the ranges and values within the explicitly stated ranges are contemplated.

Certain macromeric precursors are the crosslinkable, biodegradable, water-soluble macromers described in U.S. Pat. No. 5,410,016 to Hubbell et al, which is hereby incorporated herein by reference in its entirety to the extent it does not contradict what is explicitly disclosed. These macromers are characterized by having at least two polymerizable groups, separated by at least one degradable region.

Synthetic precursors may be used. Synthetic refers to a molecule not found in nature or not normally found in a human. Some synthetic polymers are free of amino acids or free of amino acid sequences that occur in nature. Some synthetic molecules are polypeptides that are not found in nature or are not normally found in a human body, e.g., di-, tri-, or tetra-lysine. Some synthetic molecules have amino acid residues but only have one, two, or three that are contiguous, with the amino acids or clusters thereof being separated by non-natural polymers or groups. Polysaccharides or their derivatives are thus not synthetic.

Precursors may have, e.g., 2-100 arms, with each arm having a terminus, bearing in mind that some precursors may be dendrimers or other highly branched materials. An arm on a hydrogel precursor refers to a linear chain of chemical groups that connect a crosslinkable functional group to a polymer core. Some embodiments are precursors with between 3 and 300 arms; artisans will immediately appreciate that all the ranges and values within the explicitly stated ranges are contemplated, e.g., 4 to 16, 8 to 100, or at least 6 arms.

Thus hydrogels can be made, e.g., from a multi-armed precursor with a first set of functional groups and a low molecular-weight precursor having a second set of functional groups. For example, a six-armed or eight-armed precursor may have hydrophilic arms, e.g., polyethylene glycol, terminated with primary amines, with the molecular weight of the arms being about 1,000 to about 40,000; artisans will immediately appreciate that all ranges and values within the explicitly stated bounds are contemplated. Such precursors may be mixed with relatively smaller precursors, for example, molecules with a molecular weight of between about 100 and about 5000, or no more than about 800, 1000, 2000, or 5000 having at least about three functional groups, or between about 3 to about 16 functional groups; ordinary artisans will appreciate that all ranges and values between these explicitly articulated values are contemplated. Such small molecules may be polymers or non-polymers and natural or synthetic.

Precursors that are not dendrimers may be used. Dendritic molecules are highly branched radially symmetrical polymers in which the atoms are arranged in many arms and subarms radiating out from a central core. Dendrimers are characterized by their degree of structural perfection as based on the evaluation of both symmetry and polydispersity and require particular chemical processes to synthesize. Accordingly, an artisan can readily distinguish dendrimer precursors from non-dendrimer precursors. Dendrimers have a shape that is typically dependent on the solubility of its component polymers in a given environment, and can change substantially according to the solvent or solutes around it, e.g., changes in temperature, pH, or ion content. Dendrimers are highly ordered, possess high surface area to volume ratios, and exhibit numerous end groups for potential functionalization. Embodiments include multifunctional precursors that are not dendrimers.

Some embodiments include a precursor that consists essentially of an oligopeptide sequence of no more than five residues, e.g., amino acids comprising at least one amine, thiol, carboxyl, or hydroxyl side chain. A residue is an amino acid, either as occurring in nature or derived thereof. The backbone of such an oligopeptide may be natural or synthetic. In some embodiments, peptides of two or more amino acids are combined with a synthetic backbone to make a precursor; certain embodiments of such precursors have a molecular weight in the range of about 100 to about 10,000 or about 300 to about 500. Artisans will immediately appreciate that all ranges and values between these explicitly articulated bounds are contemplated.

Precursors may be prepared to be free of amino acid sequences cleavable by enzymes present at the site of introduction, including free of sequences susceptible to attach by metalloproteinases and/or collagenases. Further, precursors may be made to be free of all amino acids, or free of amino acid sequences of more than about 50, 30, 20, 10, 9, 8, 7, 6, 5, 4, 3, 2, or 1 amino acids. Precursors may be non-proteins, meaning that they are not a naturally occurring protein and can not be made by cleaving a naturally occurring protein and can not be made by adding synthetic materials to a protein. Precursors may be non-collagen, non-fibrin, non-fibrinogen), and non-albumin, meaning that they are not one of these proteins and are not chemical derivatives of one of these proteins. The use of non-protein precursors and limited use of amino acid sequences can be helpful for avoiding immune reactions, avoiding unwanted cell recognition, and avoiding the hazards associated with using proteins derived from natural sources. Precursors can also be non-saccharides (free of saccharides) or essentially non-saccharides (free of more than about 5% saccharides by w/w of the precursor molecular weight). Thus a precursor may, for example, exclude hyaluronic acid, heparin, or gellan. Precursors can also be both non-proteins and non-saccharides.

Peptides may be used as precursors. In general, peptides with less than about 10 residues are preferred, although larger sequences (e.g., proteins) may be used. Artisans will immediately appreciate that every range and value within these explicit bounds is included, e.g., 1-10, 2-9,3-10, 1, 2, 3, 4, 5, 6, or 7. Some amino acids have nucleophilic groups (e.g., primary amines or thiols) or groups that can be derived as needed to incorporate nucleophilic groups or electrophilic groups (e.g., carboxyls or hydroxyls). Polyamino acid polymers generated synthetically are normally considered to be synthetic if they are not found in nature and are engineered not to be identical to naturally occurring biomolecules.

Some hydrogels are made with a polyethylene glycol-containing precursor. Polyethylene glycol (PEG, also referred to as polyethylene oxide when occurring in a high molecular weight) refers to a polymer with a repeat group $(CH_2CH_2O)_n$, with n being at least 3. A polymeric precursor having a polyethylene glycol thus has at least three of these repeat groups connected to each other in a linear series. The polyethylene glycol content of a polymer or arm is calculated by adding up all of the polyethylene glycol groups on the polymer or arm, even if they are interrupted by other groups. Thus, an arm having at least 1000 MW polyethylene glycol has enough $CH_2CH_2O$ groups to total at least 1000 MW. As is customary terminology in these arts, a polyethylene glycol polymer does not necessarily refer to a molecule that terminates in a hydroxyl group.

Initiating Systems

Some precursors react using initiators. An initiator group is a chemical group capable of initiating chain growth (e.g., a free radical) polymerization reaction. For instance, it may be present as a separate component, or as a pendent group on a precursor. Free radical initiator groups include thermal initiators, photoactivatable initiators, and oxidation-reduction (redox) systems. Long wave UV and visible light photoactivatable initiators include, for example, ethyl eosin groups, 2,2-dimethoxy-2-phenyl acetophenone groups, other acetophenone derivatives, thioxanthone groups, benzophenone groups, and camphorquinone groups. Examples of thermally reactive initiators include 4, 4' azobis (4-cyanopentanoic acid) groups, and analogs of benzoyl peroxide groups. Several commercially available low temperature free radical initiators, such as V-044, available from Wako Chemicals USA, Inc., Richmond, Va., may be used to initiate free radical crosslinking reactions at body temperatures to form hydrogels with the aforementioned monomers.

Metal ions may be used either as an oxidizer or a reductant in redox initiating systems. For example, ferrous ions may be used in combination with a peroxide or hydroperoxide to initiate polymerization, or as parts of a polymerization system. In this case, the ferrous ions would serve as a reductant. Alternatively, metal ions may serve as an oxidant. For example, the ceric ion (4+ valence state of cerium) interacts with various organic groups, including carboxylic acids and urethanes, to remove an electron to the metal ion, and leave an initiating radical behind on the organic group. In such a system, the metal ion acts as an oxidizer. Potentially suitable metal ions for either role are any of the transition metal ions, lanthanides and actinides, which have at least two readily accessible oxidation states. Particularly useful metal ions have at least two states separated by only one difference in charge. Of these, the most commonly used are ferric/ferrous; cupric/cuprous; ceric/cerous; cobaltic/cobaltous; vanadate V vs. IV; permanganate; and manganic/manganous. Peroxygen containing compounds, such as peroxides and hydroperoxides, including hydrogen peroxide, t-butyl hydroperoxide, t-butyl peroxide, benzoyl peroxide, cumyl peroxide may be used.

An example of an initiating system is the combination of a peroxygen compound in one solution, and a reactive ion, such as a transition metal, in another. In this case, no external initiators of polymerization are needed and polymerization proceeds spontaneously and without application of external energy or use of an external energy source when two complementary reactive functional groups containing moieties interact at the application site.

Functional Groups

The precursors may have functional groups that react with each other to form the material, either outside a patient, or in situ. The functional groups generally have polymerizable groups for polymerization or react with each other in electrophile-nucleophile reactions or are configured to participate in other polymerization reactions.

Thus in some embodiments, precursors have a polymerizable group that is activated by photoinitiation or redox systems as used in the polymerization arts, e.g., or electrophilic functional groups that are carbodiimidazole, sulfonyl chloride, chlorocarbonates, n-hydroxysuccinimidyl ester, succinimidyl ester or sulfasuccinimidyl esters, or as in U.S. Pat. Nos. 5,410,016, or 6,149,931, each of which is hereby incorporated by reference herein in its entirety to the extent it does not contradict what is explicitly disclosed herein. The nucleophilic functional groups may be, for example, amine, hydroxyl, carboxyl, and thiol. Another class of electrophiles are acyls, e.g., as in U.S. Pat. No. 6,958,212, which describes, among other things, Michael addition schemes for reacting polymers.

Certain functional groups, such as alcohols or carboxylic acids, do not normally react with other functional groups, such as amines, under physiological conditions (e.g., pH 7.2-11.0, 37° C.). However, such functional groups can be made more reactive by using an activating group such as N-hydroxysuccinimide. Certain activating groups include carbonyldiimidazole, sulfonyl chloride, aryl halides, sulfosuccinimidyl esters, N-hydroxysuccinimidyl ester, succinimidyl ester, epoxide, aldehyde, maleimides, imidoesters and the like. The N-hydroxysuccinimide esters or N-hydroxysulfosuccinimide (NHS) groups are useful groups for crosslinking of proteins or amine-containing polymers, e.g., amino terminated polyethylene glycol. Other functional groups are SG (succinimidyl glutarate), SS (succinimidyl succinate), SC (succinimidyl carbonate), SAP (succinimidyl adipate), carboxymethyl hydroxybutyric acid (CM-HBA or "CM") may be used and have esteric linkages that are hydrolytically labile. More hydrophobic linkages such as suberate linkages may also be used, with these linkages being less degradable than succinate, glutarate or adipate linkages.

An advantage of an NHS-amine reaction is that the reaction kinetics are favorable, but the gelation rate may be adjusted through pH or concentration. The NHS-amine crosslinking reaction leads to formation of N-hydroxysuccinimide as a side product. Sulfonated or ethoxylated forms of N-hydroxysuccinimide have a relatively increased solubility in water and hence their rapid clearance from the body. An NHS-amine crosslinking reaction may be carried out in aqueous solutions and in the presence of buffers, e.g., phosphate buffer (pH 5.0-7.5), triethanolamine buffer (pH 7.5-9.0), or borate buffer (pH 9.0-12), or sodium bicarbonate buffer (pH 9.0-10.0). Aqueous solutions of NHS based crosslinkers and functional polymers preferably are made just before the crosslinking reaction due to reaction of NHS groups with water. The reaction rate of these groups may be delayed by keeping these solutions at lower pH (pH 4-7).

In some embodiments, each precursor comprises only nucleophilic or only electrophilic functional groups, so long as both nucleophilic and electrophilic precursors are used in the crosslinking reaction. Thus, for example, if a crosslinker has nucleophilic functional groups such as amines, the functional polymer may have electrophilic functional groups such as N-hydroxysuccinimides. On the other hand, if a crosslinker has electrophilic functional groups such as sulfosuccinimides, then the functional polymer may have nucleophilic functional groups such as amines or thiols. Thus, functional polymers such as proteins, poly(allyl amine), or amine-terminated di-or multifunctional poly(ethylene glycol) can be used.

One embodiment has reactive precursor species with 3 to 16 nucleophilic functional groups each and reactive precursor species with 2 to 12 electrophilic functional groups each; artisans will immediately appreciate that all the ranges and values within the explicitly stated ranges are contemplated.

The functional groups may be, e.g., electrophiles reactable with nucleophiles, groups reactable with specific nucleophiles, e.g., primary amines, groups that form amide bonds with materials in the biological fluids, groups that form amide bonds with carboxyls, activated-acid functional groups, or a combination of the same. The functional groups may be, e.g., a strong electrophilic functional group, meaning an electrophilic functional group that effectively forms a covalent bond with a primary amine in aqueous solution at pH 9.0 at room temperature and pressure and/or an electrophilic group that reacts by a of Michael-type reaction. The strong electrophile may be of a type that does not participate in a Michael-type reaction or of a type that participates in a Michaels-type reaction.

A Michael-type reaction refers to the 1,4 addition reaction of a nucleophile on a conjugate unsaturated system. The addition mechanism could be purely polar, or proceed through a radical-like intermediate state(s); Lewis acids or appropriately designed hydrogen bonding species can act as catalysts. The term conjugation can refer both to alternation of carbon-carbon, carbon-heteroatom or heteroatom-heteroatom multiple bonds with single bonds, or to the linking of a functional group to a macromolecule, such as a synthetic polymer or a protein. Michael-type reactions are discussed in detail in U.S. Pat. No. 6,958,212, which is hereby incorporated by reference for all purposes to the extent it does not contradict what is explicitly disclosed herein. Examples of strong electrophiles that do not participate in a Michael-type reaction are: succinimides, succinimidyl esters, NHS-esters, or maleimides. Examples of Michael-type electrophiles are acrylates, methacrylates, methylmethacrylates, and other unsaturated polymerizable groups.

Regarding reaction rates, buffers, e.g., borate, carbonate, or phosphate salts can be added to the coating, the biomaterial, or the tissue to adjust the pH to increase the reaction rate of electrophilic functional groups such as succimide esters or maleimides.

A number of hydrogel precursors are available that could be chosen and processed into coatings with these characteristics. For instance, polyethylene glycol (PEG, a polymer with ($CH_2$—$CH_2$—O) repeats, this mer also being referred to as the PEG group) with electrophilic and/or nucleophilic functional groups may be used. These may also be used in combination with non-PEGs, e.g., di-, tri-, or tetralysine, among others; in general, see U.S. Pat. No. 7,597,882 filed Apr. 24, 2007; U.S. Pat. No. 6,605,294 filed Aug. 14, 1998; U.S. Pat. No. 6,566,406 filed Dec. 3, 1999; U.S. Pat. No. 6,703,047 filed Feb. 2, 2001; U.S. Pat. No. 7,220,270 filed Jan. 13, 2004; and U.S. Ser. No. 11/406,791 filed Apr. 19, 2006, which are hereby incorporated by reference herein in their entireties.

Precursors that are non-PEG based compounds are included. Some precursors are free of the PEG group ($CH_2$—$CH_2$—O), some are free of more than one PEG group, and some are free of all ethers. Other precursors have more than one PEG group but do not have more than two of them adjacent to each other. Some precursors have less than 500, 400, 300, 200, 100, or 50 in molecular weight of PEG groups, while others have between 40-500 molecular weight of PEG groups; artisans will immediately appreciate that all the ranges and values within the explicitly stated ranges are contemplated.

Precursors may be prepared in a purified preparation that has a high concentration of the precursors, i.e., more than about 75% w/w. Such preparations may be prepared with a greater purity, e.g., more than about 90%, 95%, or 99% w/w. Artisans will immediately appreciate that all the ranges and values within the explicitly stated ranges are contemplated. More than one type of precursor may be mixed together to form the purified preparation as appropriate. One advantage of using such a preparation is that it may be used directly without dilution, e.g., when crosslinking other precursors.

Some precursors preparations may be prepared to be essentially free of water. For instance, dry reagents may be used, or the crosslinker may be purified through precipitation or lyophilization processes.

The adherence, strength and swelling of the coating can be controlled by the amount, pattern and type of precursor in the coating. Coating is a term that denotes a layer on an object. The term coating or layer may be used interchangeably, and a plurality of layers being collectively referred to as a coating when appropriate. In contrast, other constructs, e.g., sheaths, sleeves, membranes, and molded objects, can be manufactured separately from a particular device and are not coatings and are not layers. For example, a sleeve, sheath, or membrane requires a certain minimum of mechanical robustness so as to maintain its identity before being associated with an object. Further, a process of coating creates an intimacy of contact between the coating and the device that is often desirable; for this reason, some processes involve coatings instead of other manufacturing procedures.

It is recognized, however, that a coating can have variable characteristics. Thus a coating may be discontinuous with a surface at some points and still retain its characteristic as a coating. Coatings may also be formed of a single layer, or a plurality of layers. Coatings, and layers, can have a variable thickness, variable composition, variable chemical properties. Coatings, and layers, may cover all or a portion of a surface. Layers may, e.g., be superimposed upon other layers to create a coating.

Layers may be made from a single type of precursor or a plurality of precursors. Some layers are useful for providing a foundational layer that contacts a device and serves to anchor subsequently applied layers. For example, a first layer with reactive functional groups may be applied to a device, and a subsequent layer may be applied to the foundational layer.

A therapeutic agent may be associated with a foundational layer, the subsequently applied layer, or both. Therapeutic agents may be associated with a precursor before the precursor is applied to a device. The precursor may be prepared and then exposed to a solution containing a solvent for the agent. The agent and the precursor are allowed to interact, and the agent becomes associated with the precursor. Alternatively, a therapeutic agent may be added to a precursor melt or the therapeutic agent may be exposed to a precursor at essentially the same time that the agent and the precursor are essentially simultaneously applied to a device. The precursor and the agent may be in the same or different solvent, or alternatively, in the same or different non-solvents that are carrier agents. The application of one or both of the precursor and the agent in a non-solvent would affect the resultant layer. Therapeutic agents may be associated with a layer after the layer is applied to a device. One method is to expose the layer to a mixture containing the agent. The mixture may include a relatively good solvent for both the agent and the layer so that the layer is swelled and the agent migrates therethrough. When the solvent is removed, the agent is left in the layer.

Coating Formation

Processes for forming a layer on an object, e.g., a backing, a biomaterial, or a medical device, may include applying a composition to a device by spraying, or by dipping the device into a composition for forming a polymeric layer. Materials taught herein may be formed in layers upon a medical device, including a layer that covers all of a device, a discontinuous layer that covers a portion of the device, and layers upon other layers. Layers that contact each other may be crosslinked to each other, e.g., by covalent crosslinks between polymers in the layers.

Creation of dry precursor coatings may be done in any of several ways. The components may be melted together and then a thin coating applied to the biomaterial that is to be adhered to the site. Melting points for such precursors would be chosen to provide for the material to be a solid at room temperature (about 20° C.) and/or at physiological temperature (about 37° C.). For instance, precursors may be selected so that a thin coating of melted PEG ester and amine precursors may be applied to one or both sides of a lyophilized hydrogel biomaterial and allowed to come to room temperature, at which point the coating is solidified.

Another approach to make a coating is to use a blend of two or more precursors in a dry powder form. This dry powder form can be generated by a dry blending process or, if stability does not prove to be an issue, by a solvent based blending process (such as methanol or water) as a co-solvent, followed by drying. The powder can be mixed with binding agents to prepare a coating.

One embodiment of an adhesive coating is made by mixing of polyethylene glycol (PEG) reactive esters (e.g., succinimide esters and/or maleimides) and PEG amines (e.g., equimolar amounts of esters and amines). Salt forms of PEG amines may be used instead of free PEG amines, for stability purposes, since they withstand storage and sterilization better and have a lower tendency to spontaneously pre-react. An alternative embodiment is a layering of the precursors. Thus a first layer of one precursor is applied to the device and a second layer of another precursor is applied thereupon. Or different ratios of the precursors could be applied in various layers. Accordingly, a first layer could comprise or consist of precursors with nucleophilic groups and a second layer could comprise electrophilic groups.

Full and Partial Coatings, Uncoated Portions of Materials

Figure 2B:
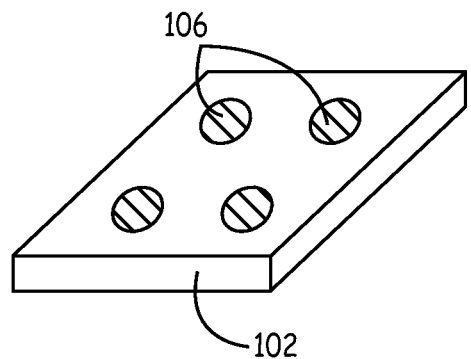
FIG. 2B depicts a partially coated biomaterial with a coating disposed as a plurality of blebs.
Figure 2C:
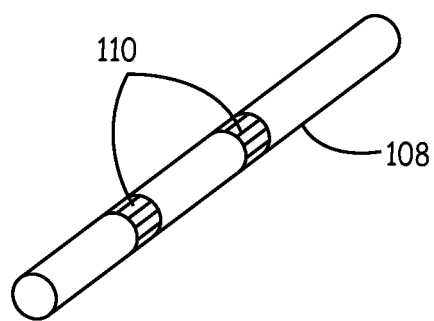
FIG. 2C depicts a partially coated biomaterial with a coating disposed as a plurality of rings.

FIG. 2A depicts biomaterial sheet 102 with stripes of adhesive 104. FIG. 2B depicts biomaterial sheet 102 with blebs 106 of coating. A bleb is a term used herein to denote a deposit on a relatively much larger and continuous field, with a plurality of blebs being deposits not connected to each other: for example, a drop or dot, be it rounded or irregular in shape. Examples of bleb volumes are 0.1 to 100 µl; artisans will immediately appreciate that all the ranges and values within the explicitly stated ranges are contemplated. FIG. 2C depicts a biomaterial rod 108 with a plurality of stripes 110.

Figure 3A:
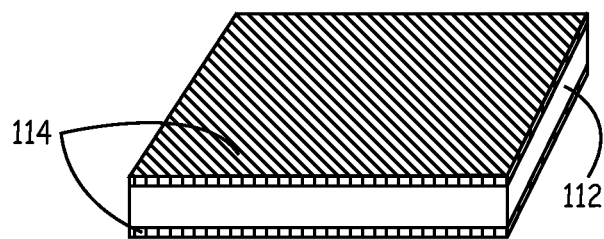
FIG. 3A depicts a biomaterial coated on each of two faces.
Figure 3B:
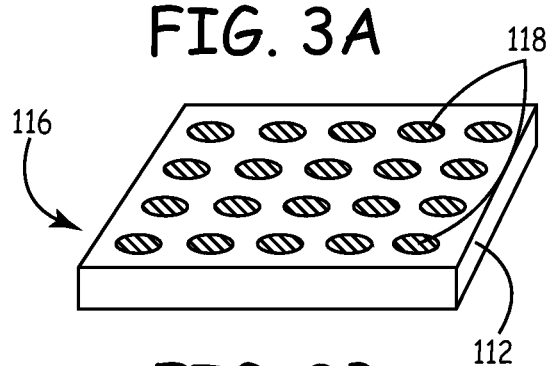
FIG. 3B depicts a biomaterial partially coated on each of two faces, with the coating being a plurality of blebs.
Figure 3C:
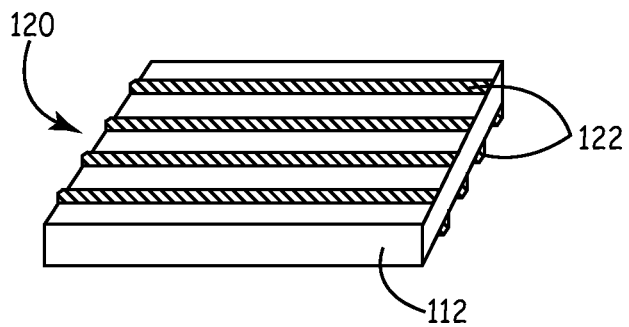
FIG. 3C depicts a biomaterial partially coated on each of two faces, with the coating being a plurality of stripes.

FIG. 3A depicts biomaterial sheet 112 with two faces separated by a thickness with a continuous coating 114 on each of the two faces. FIG. 3B depicts biomaterial sheet 112 with two faces separated by a thickness with a discontinuous and partial coating 116 on each of the two faces, with the discontinuous coating comprising a plurality of blebs 118 that are approximately elliptical or circular. FIG. 3C depicts biomaterial sheet 112 with two faces separated by a thickness with discontinuous coating 120 on each of the two faces, with the discontinuous coating 120 comprising a plurality of domains that are stripes 122.

The coatings may be disposed in various patterns, e.g., dots, stripes, dashed stripes, checkerboard, or wavy stripes. The patterns are disposed across a surface area with between, e.g., 10% and 90% coverage; artisans will immediately appreciate that all the ranges and values within the explicitly stated ranges are contemplated. For instance in FIG. 3C the stripes overlay about a third or a half the pattern surface area. The choice of the pattern and the percent coverage of the surface area can be used to tune the rate of dissolving (and thus bonding) of precursors, the exposure of the biomaterial to physiological fluids, e.g., as in accelerating or decelerating swelling of a hydratable and swellable biomaterial.

Figure 4A:
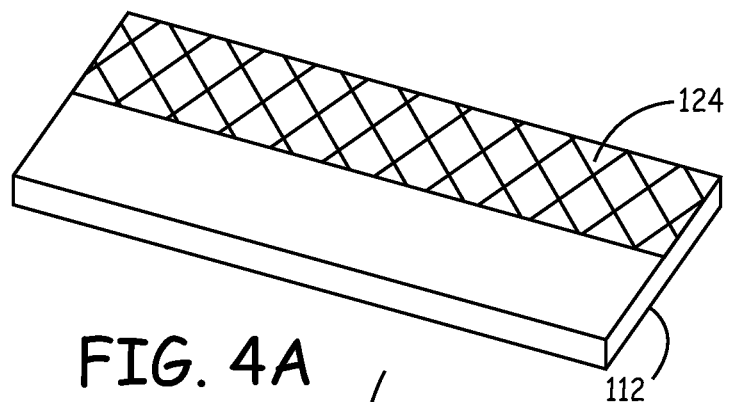
FIG. 4A depicts a biomaterial sheet partially coated on a longitudinal half.
Figure 4B:
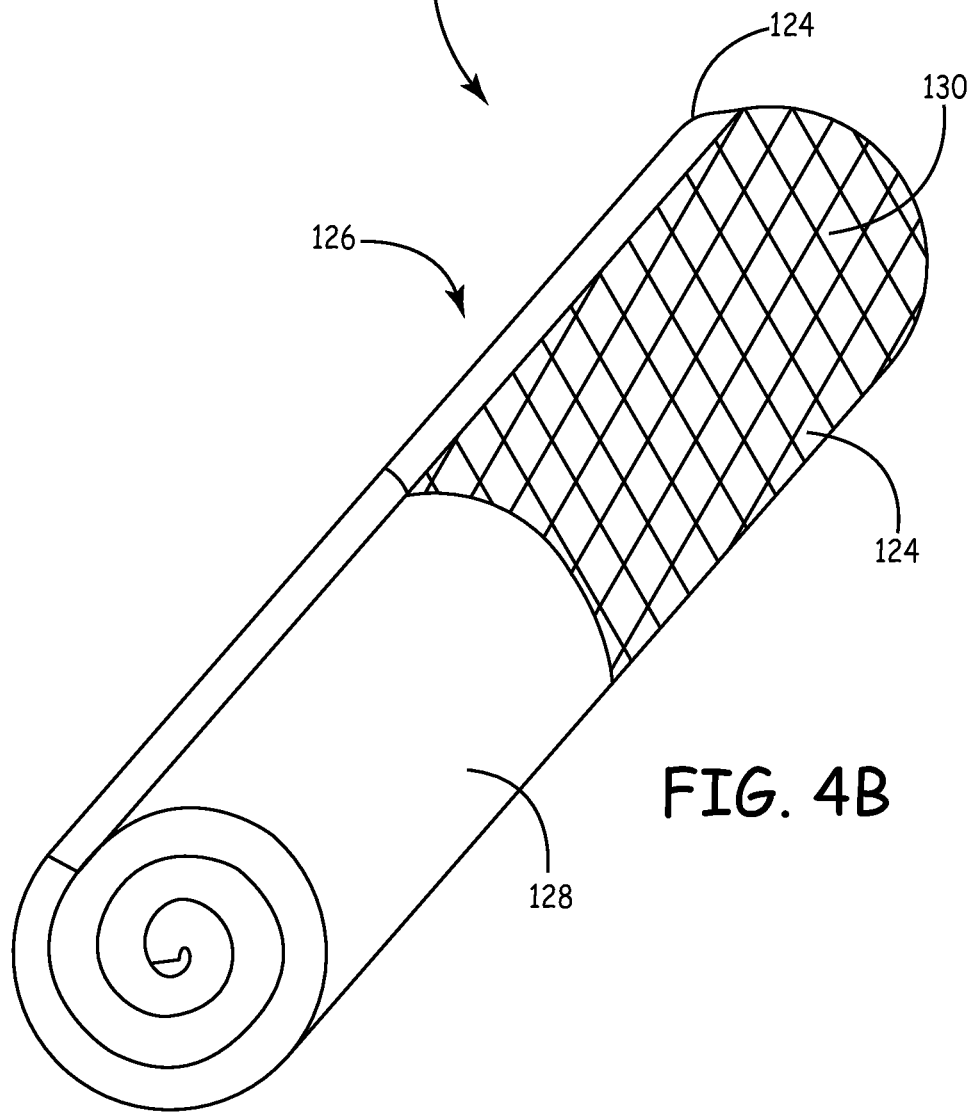
FIG. 4B depicts the material of FIG. 4A in a rolled configuration.

FIG. 4A depicts biomaterial 112 having a partial and continuous coating 124. The adhesive coating 124 is formed on one portion of biomaterial 112 that is then rolled to form plug 126 with a first half or other portion 128 that is free of coating and a second half or other portion that is coated 130, as at FIG. 4B. The coating 124 in this example extends fully around the circumference of the coated portion.

A non-continuous (discontinuous) coating (e.g., dots, stripes) allows for the non-coated material to react directly with its environment. In the case of a material that readily absorbs fluid, an uncoated portion allows for blood or other fluid absorption into the material. A swellable material would thus swell more readily and rapidly when it is uncoated. Accordingly, a discontinuous coating (e.g., dots, stripes) can enhance fluid absorption. In the first place, the fluid has enhanced access to the coating itself. In the second place, the underlying biomaterial may be chosen as a hydratable material that fills and/or swells in response to fluid. A discontinuous coating provides enhanced access to such a material, improving its swelling ability to fill the track and/or apply compressive force to a vascular puncture. A swelling material causes the hydrogel coating to be in close proximity to the tissue.

The coating and/or underlying biomaterial can be prepared with an open structure that facilitates rapid fluid uptake. A discontinuous coating that has channels or spaces that allow fluid access to the coating accelerates dissolution of the precursors therein. The precursors may also be lyophilized to provide a porous and permeable structure that facilitates fluid uptake. For example, the precursors may be prepared as a solution that is frozen and then lyophilized.

Alternatively, the precursors may be prepared in a solution that is rapidly removed by evaporation, either by use of a volatile solvent (small alcohols or volatile organic solvents) and/or with a low-pressure. In contrast, a drying-out process at ambient or comparable conditions is not rapid evaporation and can provide opportunity for aggregation that tends to resist rapid dissolution. Dry chemistry protocols that minimize exposure to water generally assist in preparing precursors and coatings.

If a coating is found to interfere with the unfurling or opening of a material substrate that is intended to transition from a compact to an expanded position or shape, a thin interfacial layer of a releasing agent may be applied. A releasing agent may be generally applied for these or other reasons. Such releasing agents may include finely powdered sugars, salts, liquid PEGs, pharmaceutically acceptable oils, or other pharmaceutically acceptable vehicles.

Buffers may be used in combination with a coating. The buffers may be mixed with the precursors in a layer or provided as a separate layer on or under the precursor layer(s). A buffer embodiment is a carbonate, phosphate, or borate buffer effective to increase concentration around the applicator above neutral to accelerate the reaction. In some embodiments, the pH is raised to a value between pH 8.5 and 10; artisans will immediately appreciate that all the ranges and values within the explicitly stated ranges are contemplated, e.g., more than about pH 8.5, more than about pH 9, from about pH 8 to about pH 10. One measure of the effectiveness of the buffer is to test the rate of the reaction and/or quality of the seal when the buffer is used: in the case of a track, the precursors can be tested with and without the buffer to determine if the pH is effectively being raised as indicated by changes to the precursors' activity. An embodiment of the buffer is a powder mixed with a binding agent. A binding agent may be chosen that dissolves in a physiological fluid. Examples of binding agents are polyethylene glycols (e.g., 1000-30,000 MW; artisans will immediately appreciate that all the ranges and values within the explicitly stated ranges are contemplated, e.g., 10,000) or polysaccharides. Further, in some embodiments, the buffer and binding agent mixture is chosen to dissolve more rapidly that the precursor reservoir on the applicator. For instance, a PEG binding agent may be chosen that has a lower MW than a PEG-containing precursor on the applicator.

Materials that Receive a Layer

Some embodiments involve a coated biomaterial. Many biomaterials may be adapted for coating. Collagens are degradable and generally well-accepted in the medical community and may be processed into desired shapes. Other naturally-derived biomaterials include gelatin, hyaluronic acid, fibrin, fibrinogen, and polysaccharides. Synthetic materials (not found in nature and not processed from materials found in nature) may alternatively be used, as described above. In general, the material is to be processed into a shape that is suited to the application, so that it fits into the tissue site and satisfies the intended use, such as stopping flow from a blood vessel and/or from tissue around a track.

This biomaterial may be made of a biodegradable material. Lyophilized biocompatible materials are suited for this purpose, since they are biocompatible, have a history of human use in this setting, and can also swell and aid in the vascular closure. Such materials can be used to simply and rapidly seal small bore sites. Such existing technology works well without adhesive adjuncts or coatings for the smaller holes, but with access sites of about 8 F and larger, the potential exists for plugs that are secured by swelling to be dislodged and result in the consequent development of a hematoma. U.S. Ser. No. 11/465,791 filed Aug. 18, 2006, which discloses exemplary materials and methods for making them, is hereby incorporated by reference herein in its entirety.

The biomaterial itself may be made of components that are described herein for use as precursors. The coating may be the same as the biomaterial but would normally have different characteristics that are suited to its specialized function. Accordingly, such materials may be reacted with each other outside the body to prepare a biomaterial and prepared with a shape as desired.

Lyophilized hydrogels made from PEG precursors are well suited for the biomaterials to be used as plugs, since they are biocompatible, have a history of human use in this setting, and can also swell to aid in the vascular closure. PEG hydrogel precursors may be selected for a thin coating. For instance, melted PEG ester and amine precursors may be applied to one or both sides of the lyophilized hydrogel biomaterial and allowed to come to room temperature, at which point the coating is solidified.

The biomaterial may be water-degradable, as measurable by the hydrogel being dissolvable in vitro in an excess of water by degradation of water-degradable groups. This test is predictive of hydrolytically-driven dissolution in vivo, a process that is in contrast to cell or protease-driven degradation. The hydrogels can be selected to be absorbable over days, weeks, or months, depending on the drug selected, disease being treated, the duration for release that is needed, and the release profile of the specific drug selected.

The biodegradable linkage may be water-degradable or enzymatically degradable. Illustrative water-degradable biodegradable linkages include polymers, copolymers and oligomers of glycolide, dl-lactide, l-lactide, dioxanone, esters, carbonates, and trimethylene carbonate. Illustrative enzymatically biodegradable linkages include peptidic linkages cleavable by metalloproteinases and collagenases. Examples of biodegradable linkages include polymers and copolymers of poly(hydroxy acid)s, poly(orthocarbonate)s, poly(anhydride)s, poly(lactone)s, poly(aminoacid)s, poly(carbonate)s, poly(phosphonate)s.

If it is desired that the biocompatible crosslinked polymer be bioresorbable or absorbable, one or more precursors having biodegradable linkages present in between the functional groups may be used. The biodegradable linkage optionally also may serve as the hydrophilic core of one or more of the precursors. For each approach, biodegradable linkages may be chosen such that the resulting biodegradable biocompatible crosslinked polymer will degrade or be absorbed in a desired period of time.

The crosslinked hydrogel degradation will generally proceed by the water-driven hydrolysis of the biodegradable segment when water-degradable materials are used. If polyglycolate is used as the biodegradable segment, for instance, the crosslinked polymer could be made to degrade in about 1 to about 30 days depending on the crosslinking density of the network. Similarly, a polycaprolactone based crosslinked network can be made to tend to degrade in about 1 to about 8 months. The degradation time generally varies according to the type of degradable segment used, in the following order: polyglycolate<polylactate<polytrimethylene carbonate<polycaprolactone. Polymers that include ester linkages may also be included to provide a desired degradation rate, with groups being added or subtracted near the esters to increase or decrease the rate of degradation. Thus it is possible to construct a hydrogel with a desired degradation profile, from a few days to many months, using a degradable segment.

Use of a Coated Material

An embodiment of a system for using a coated material is set forth in FIG. 5. At FIG. 5A, an iatropic tract 200 has track 202 and puncture 204 in blood vessel 206. A balloon 205 has been inflated via guidewire or larger gauge introducer wire 207 using means known to artisans. FIG. 5B depicts plug 218 that has uncoated proximal portion 220 and partially coated distal portion 222. A coating comprising matrix precursors is provided as a plurality of blebs 224. The plug has axial bore 209 for passage over a guidewire, hollow wire, catheter, or other elongate member. A guidewire is a hollow wire with an outer dimension of less than about 0.08 inches. Hollow wire is a broader term referring to guidewires or larger wires with an inner bore. FIG. 5C depicts applicator 208 loaded with plug 218. Applicator 208 has pusher rod 210 with handle 212 that is received by delivery sheath 214 that has handle 216. Sheath 214 is preloaded with plug 218. Pusher rod 210 has a first deployment position and a second tamping position. Wire 207 passes through plug 218 and applicator 208. With pusher rod 210 in the deployment position, sheath 214 is introduced into track 202 to place its distal tip 223 proximate puncture 204. While pusher rod 210 is held stationary or forced downwardly to apply force against plug 218, a user pulls handles 216 upwardly, as at FIG. 5D and arrows D, to move distal tip 223 upwardly relative to the user to expose coated distal portion 222.

Figure 5A:
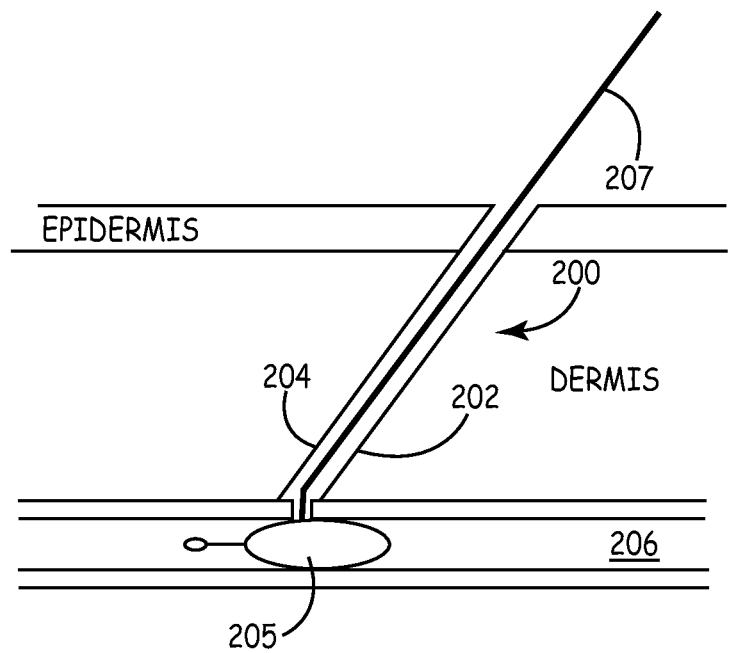
FIG. 5A depicts an elongate member attached to an occluding device positioned in a track and blood vessel.
Figure 5B:
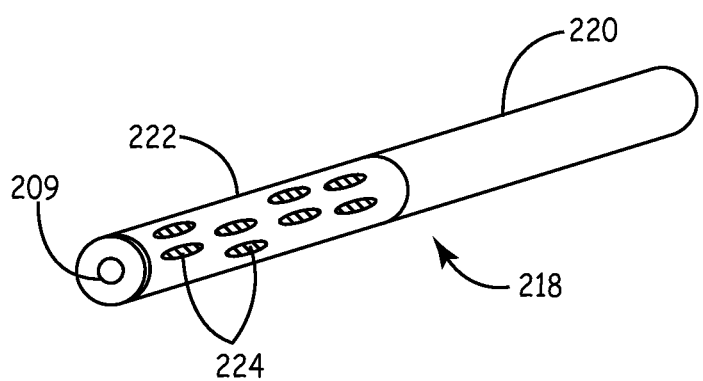
FIG. 5B depicts a plug with a partial and discontinuous coating on a half of the plug.
Figure 5C:
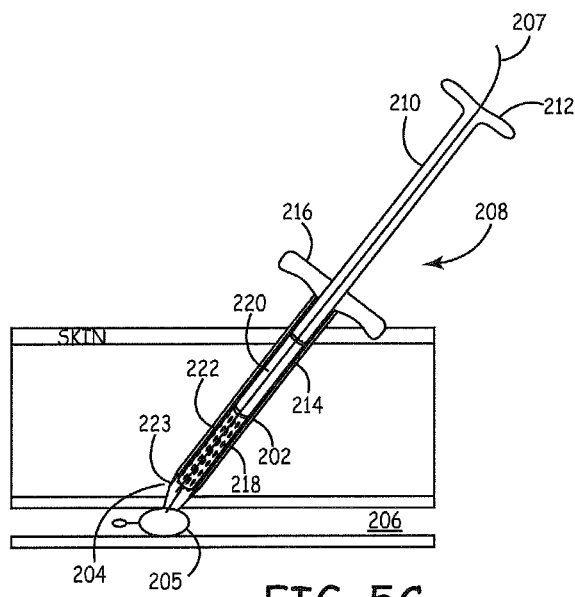
FIG. 5C depicts a delivery apparatus and the plug of FIG. 5B deployed over the elongate member of FIG. 5A.
Figure 5D:
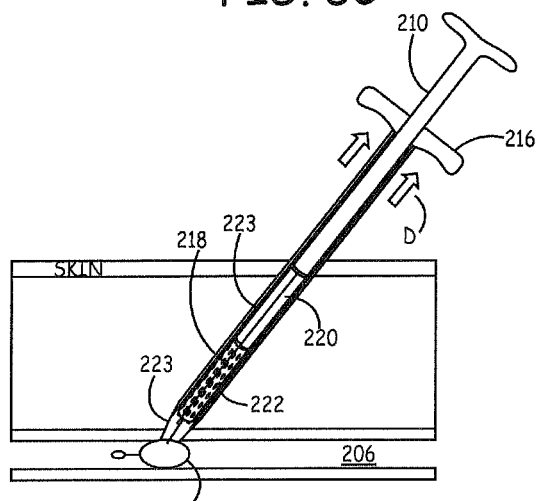
FIG. 5D depicts the apparatus of FIG. 5C in a process of delivering the plug of FIG. 5B.
Figure 5E:
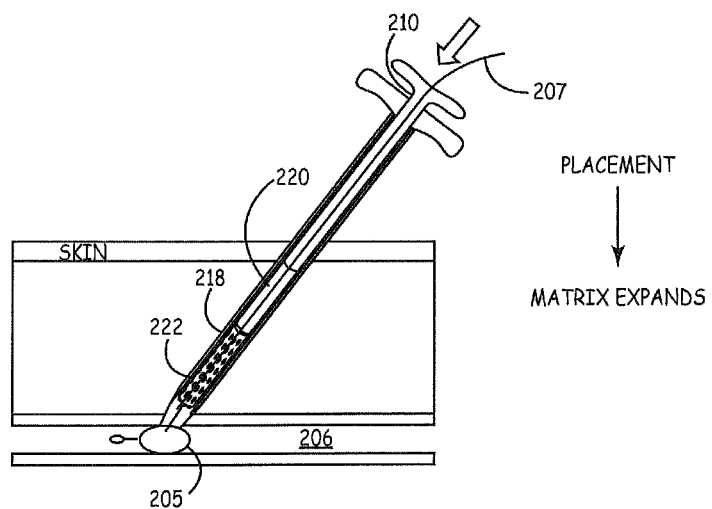
FIG. 5E depicts the apparatus of FIG. 5C in a further stage of a process of delivering the plug of FIG. 5B.

At FIG. 5E, the user pushes pusher rod 210 downwardly to compress plug 218. The coated and uncoated portions of the plug are firmly held against the tissue for a predetermined amount of time, e.g., 10-120 seconds (artisans will immediately appreciate that all the ranges and values within the explicitly stated ranges are contemplated). The coating dissolves and physiological fluids access the uncoated plug portions. A swellable plug swells as a result, and contribute to hemostasis at the plug. The balloon is subsequently deflated through the hollow wire and withdrawn through the plug. Swelling may contribute to resist devasation (forcing of the plug out of the track). Adhesion of the coating to the tissue further contribute to resist devasation, i.e., to promote stable positioning. Some embodiments may provide a plug biased to open, e.g., a plug made of a sheet furled about its axis so that it is biased to unfurl, or a compressed and resilient material. The term plug is a broad term that refers to a material blocking a channel, and includes rods, hollow tubes, dumbbell shapes, cones, and so forth. The plug is preformed outside the body unless in situ formation is indicated.

As is evident, the plug does not enter the blood vessel, although it could be so placed. The plug achieves closure proximate the blood vessel without actually entering it. The plug can engage the adventitia or be proximate the adventitia, i.e., about 1-5 mm away from the adventitia (artisans will immediately appreciate that all the ranges and values within the explicitly stated ranges are contemplated). The closure at such positions allows for natural clotting processes to take place at the blood vessel puncture.

Figure 5F:
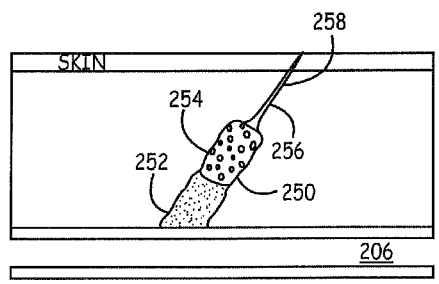
FIG. 5F is an alternative embodiment of the plug of FIG. 5B as deployed in a track.

Alternatively, FIG. 5F depicts an alternative embodiment, with plug 250 that has uncoated distal portion 252 and partially coated proximal portion 254. This configuration will allow for adherence of the coated plug, preventing expulsion due to blood pressure in the vessel, while ensuring dissolved and polymerized coating stay away from the vessel arteriotomy and intravascular space. In the depicted example, track 256 has proximal portion 258 unsealed, with blood oozing into the upper portion of the track and congealing.

Another embodiment for using a coated material as a fully implanted device for vascular closure is depicted at FIG. 6. FIGS. 6A and 6B depict applicator 300 extending from catheter 302. Applicator 300 has plug 304, inner mandrel 306, and outer mandrel 308. Plug 304 has a biomaterial sheet 310 with coating 312. The coating may be a coating as described herein, for instance one or more dried precursors that form a matrix when exposed to a physiological fluid. Sheet 310 has opening 314. Opening 314 may be sized to accommodate a guidewire or a larger gauge hollow wire. Sheet 310 is disposed on a plurality of struts 316. Struts 316 are connected at one distal portion to inner mandrel 306 and at another proximal portion to outer mandrel 308. Axial bore 318 passes through applicator 300 and, as depicted, may be coaxial with opening 314. As shown in FIGS. 6C-6D, the relative movement of inner mandrel 306 and outer mandrel 308 moves struts 316 from a storage position to a deployed position, arrow D, wherein the struts are moved radially outwards, arrow D'.

Figure 6A:
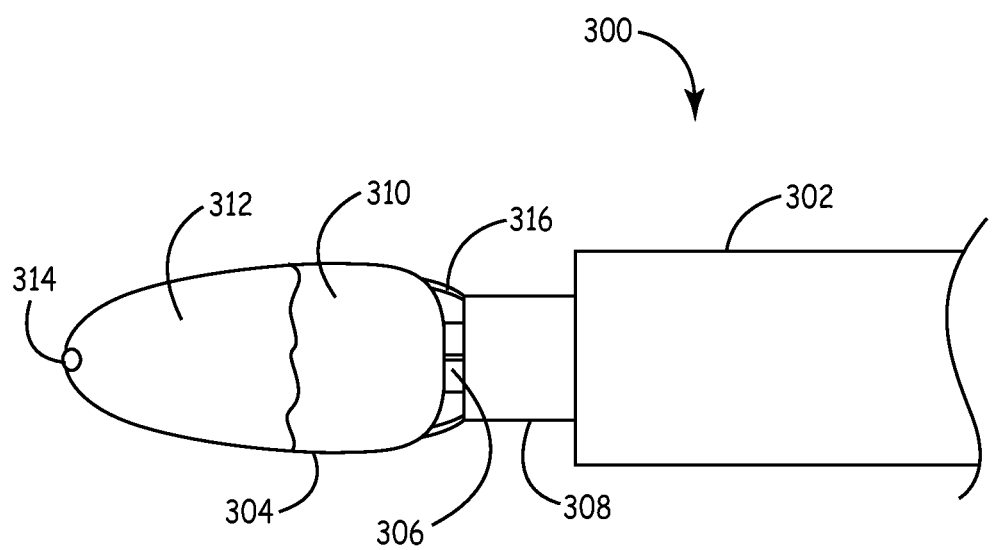
FIG. 6A depicts a delivery apparatus for a biomaterial plug with a substantially planar shape.
Figure 6B:
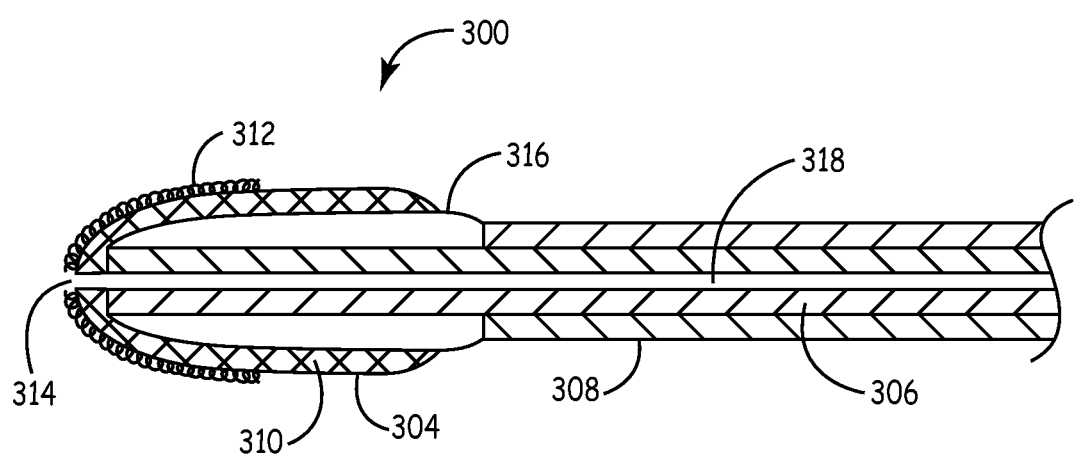
FIG. 6B is a longitudinal cross-section of the apparatus of FIG. 6A.
Figure 6E:
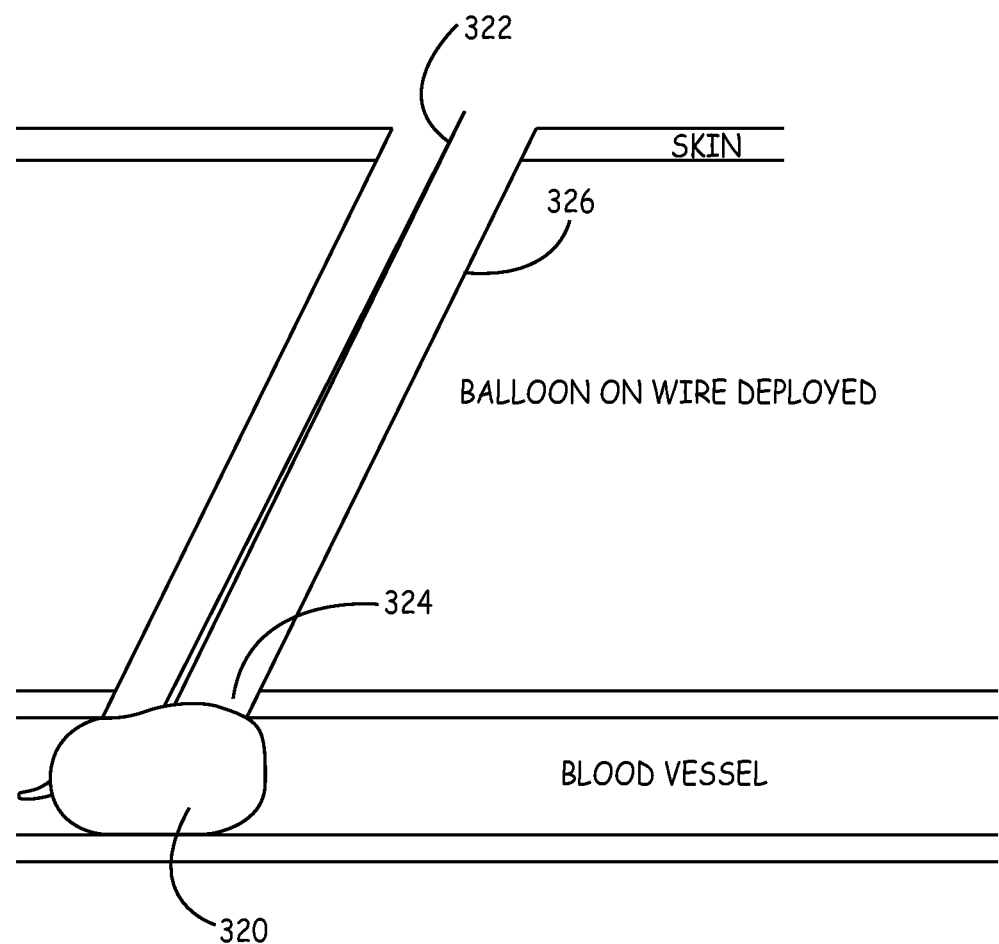
FIG. 6E depicts an elongate member attached to an occluding device positioned in a track and blood vessel.
Figure 6F:
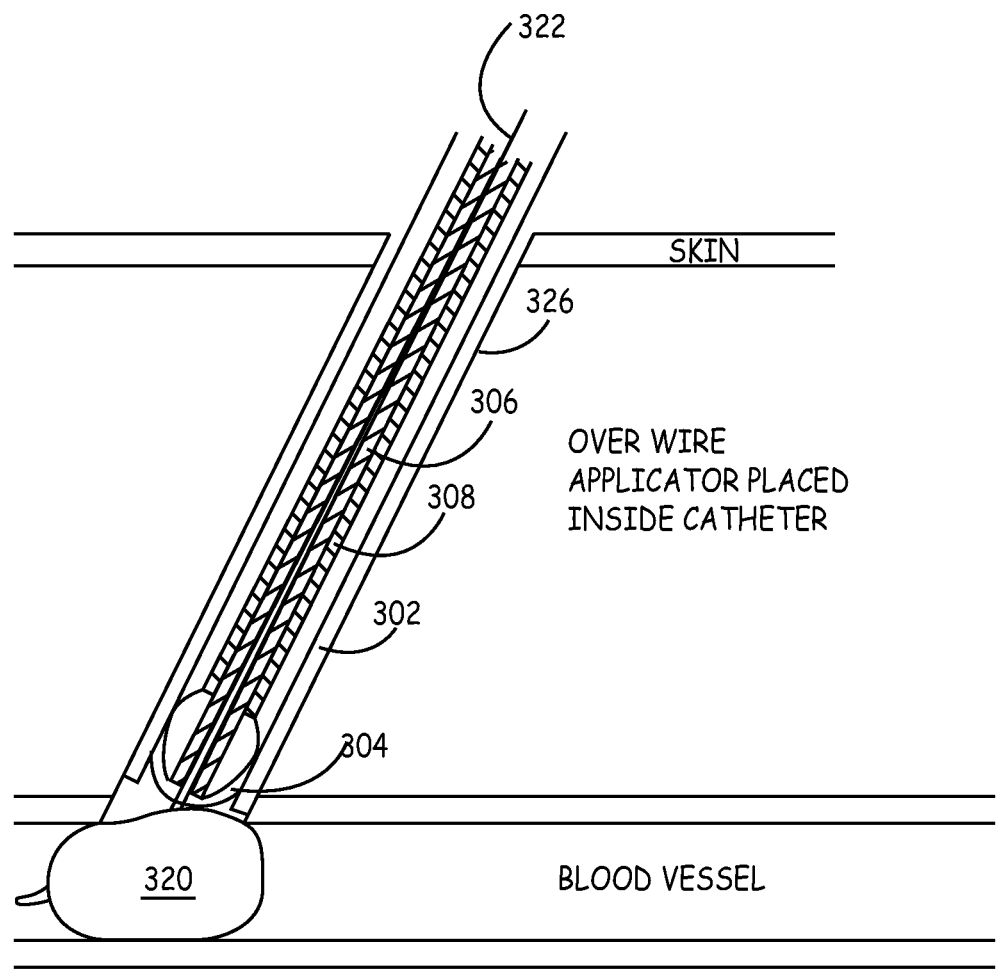
FIG. 6F depicts a cross-section of the apparatus of FIGS. 6A and 6B as deployed over the elongate member of FIG. 6E.
Figure 6G:
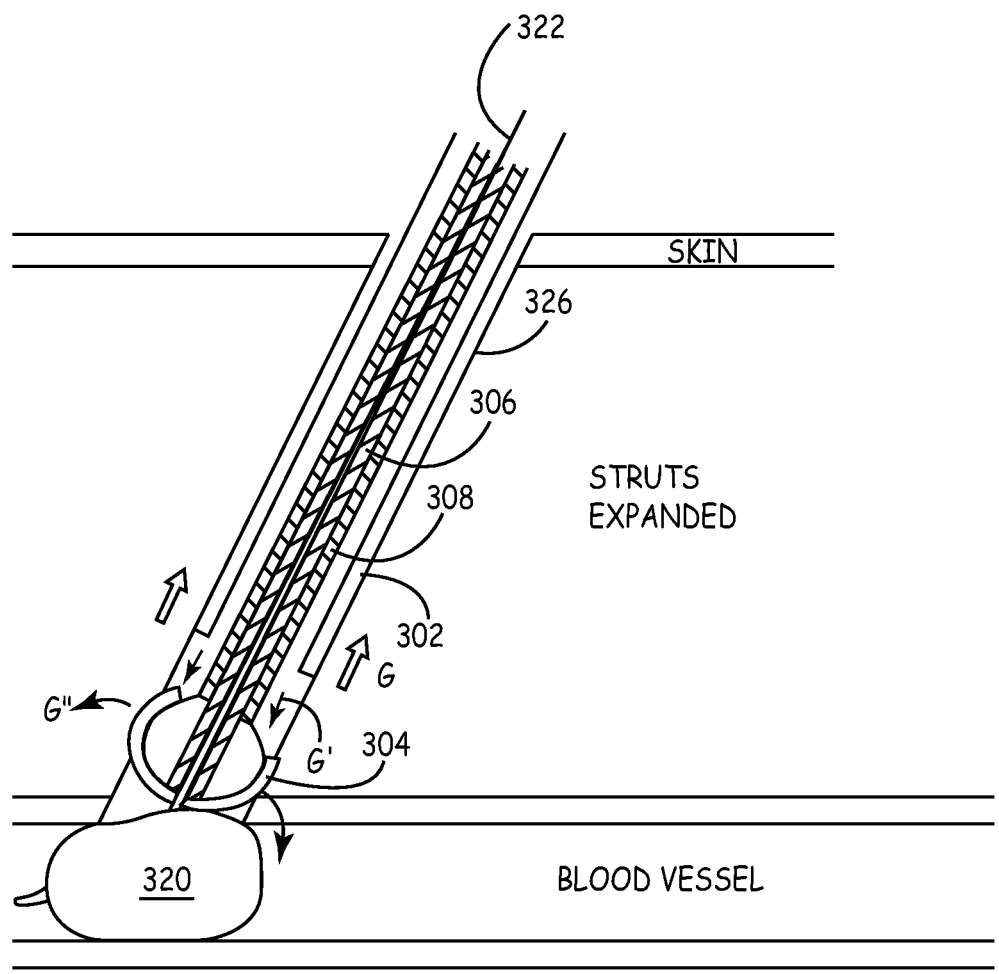
FIG. 6G depicts a process of expanding the radially expanding member of the embodiment of FIG. 6F to deploy the biomaterial in the track.
Figure 6H:
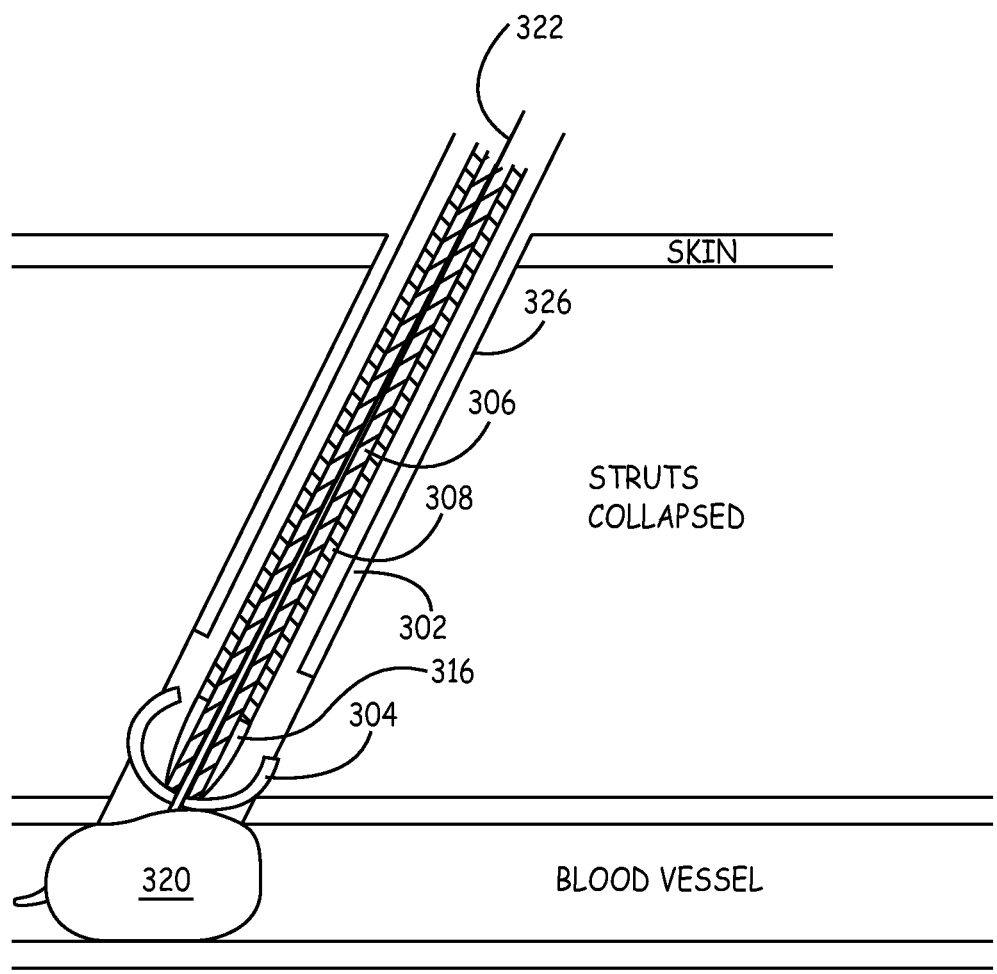
FIG. 6H depicts a process of using the embodiment of FIG. 6F to deploy the biomaterial in the track.

FIG. 6E depicts balloon 320 that has been inflated via guidewire, larger gauge hollow wire, or catheter 322 using means known to artisans to place balloon 320 across vascular puncture 324 in track 326. Applicator 300 is passed over wire 322 into track 326, inside catheter 302, FIG. 6F. Catheter 302 is positioned proximate balloon 320, and moved upwardly as at arrows G in FIG. 6G, to expose plug 304. Outer mandrel 308 is moved downwardly as at arrow G' relative to inner mandrel 306 to force struts 316 radially outwards, as at arrows G". Sheet 310 and coating 312 are forced against the surrounding tissues and held for a predetermined time, e.g., 10 to 200 seconds (artisans will immediately appreciate that all the ranges and values within the explicitly stated ranges are contemplated). Track 326 may be thereby deformed as compression is applied. At FIG. 6H, the struts 316 are moved from the deployed position to the storage position by relative movement of the mandrels. Plug 304 remains in place. The applicator is optionally rotated to help release the struts, e.g., from 45 to 360 degrees (1 turn) or several turns (artisans will immediately appreciate that all the ranges and values within the explicitly stated ranges are contemplated). At this juncture, the applicator and balloon and guidewire may be removed.

Figure 6I:
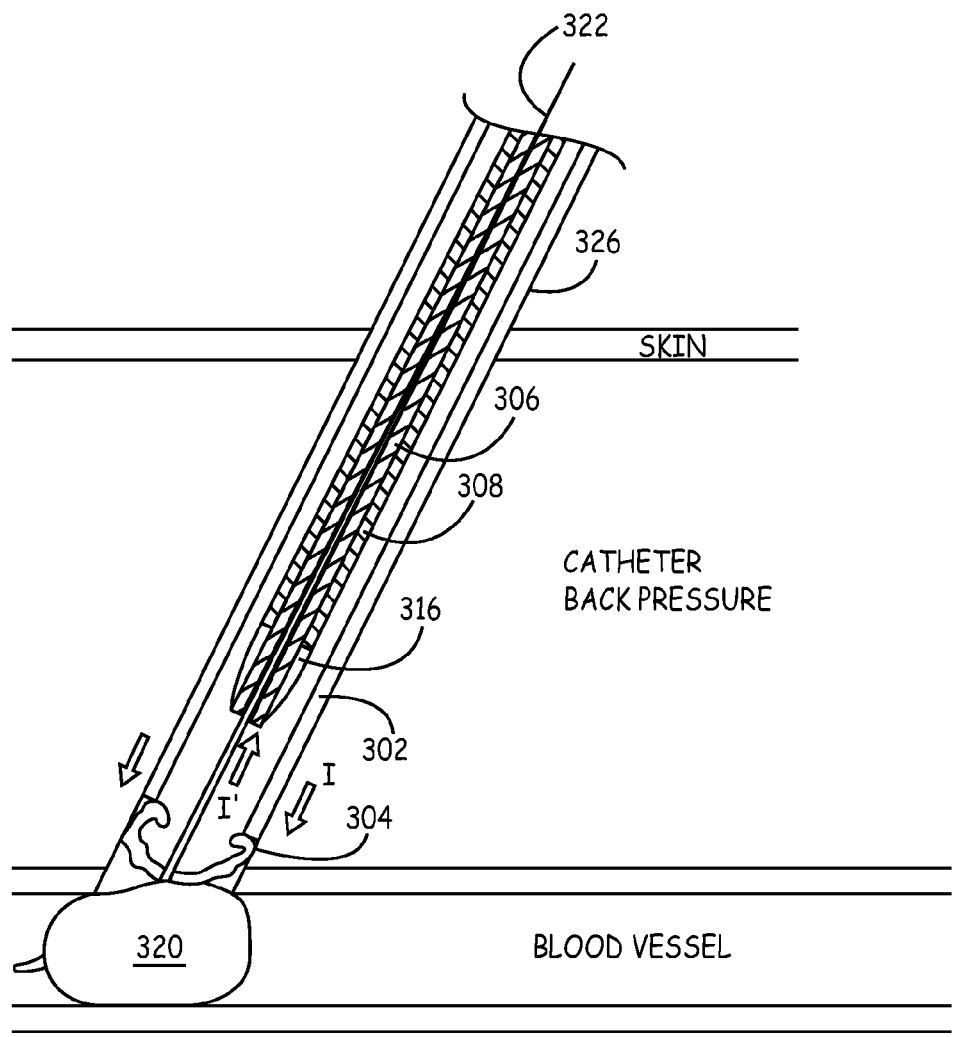
FIG. 6I depicts a further process of using the embodiment of FIG. 6F to deploy the biomaterial in the track.
Figure 6J:
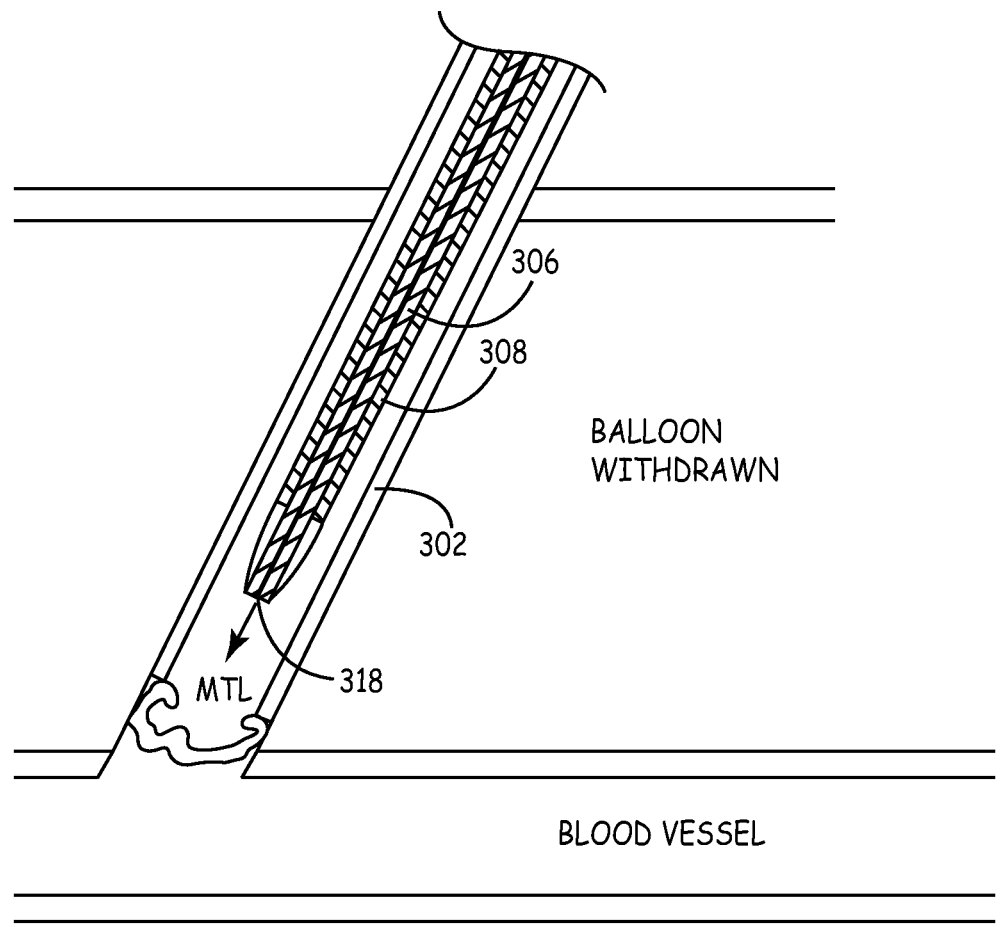
FIG. 6J depicts a further, optional, process of using the embodiment of FIG. 6F to deploy the biomaterial in the track.
Figure 6K:
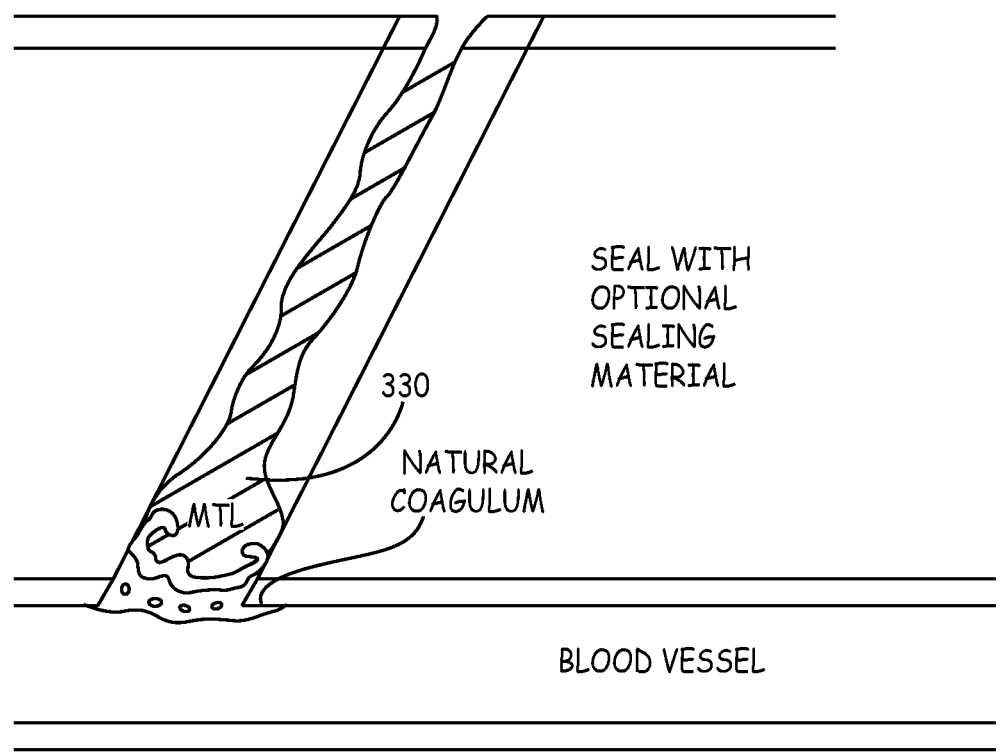
FIG. 6K depicts an outcome of the process depicted at FIG. 6J.

A further optional step is to move catheter 302 downwardly, as at arrow I in FIG. 6I, to compress and/or hold plug 304 in place while balloon and/or guidewire and/or applicator are removed, as at arrow I'. FIG. 6J depicts another optional step, wherein materials are introduced via axial bore 318 after the balloon and hollow wire are removed. In this step, one or more matrix-forming precursors are introduced through the applicator into a space proximal the plug and in the track. Precursors as described herein may be used, and may be introduced in a solution. The plug prevents entry of the precursors into the blood vessel. The catheter and applicator may be positioned as depicted or otherwise (or altogether removed, in the case of catheter 302). FIG. 6K depicts the track after this optional step, with matrix 330 in place. The matrix may be a matrix as described herein, e.g., covalently crosslinked and/or a hydrogel. The matrix may be positioned through all or a portion of the track, e.g., the most distal half, substantially throughout, or in the proximal half. The matrix may be created in situ from one or more precursors.

In the context of vascular closure, the term proximal means close to the user that is deploying the device, and distal means relatively farther away and closer to the blood vessel. Radially outwards means a movement from a center of the track towards the track periphery, as in an axial umbrella opening-up to encounter the lumen of the track. Downwards means towards the blood vessel and upwards means away from the blood vessel.

The plug may thus be a sheet with a full or partial coating on one side or both sides (and/or on the edges of the sheet). The coating may be in a pattern. The coating may be made of one or more precursors set forth herein. The sheet may be made of a material as described herein, and includes biodegradable and non-degradable materials.

The applicator may employ other mechanisms to deploy the sheet or other plug shape. Further, various occlusive devices and deployment systems may be used to tamponade a puncture, with the balloons herein being described as one type of occlusion member for exemplary purposes. Alternatives include pledgets or temporary plugs, e.g, as a in U.S. Pub. Nos. 2006/0100664 or 2006/0034930, which are hereby incorporated by reference herein for all purposes to the extent they do not contradict what is explicitly disclosed herein. Artisans reading this application in its entirety will appreciate the broad applicability of the coated materials for use in a variety of puncture closure systems.

The biomaterials for the plug, the sheet, or other matrix materials, may be provided with a shape suited to the particular application. Such shapes include, for example, rods, cylinders (hollow rods), teardrop-shapes, a tube, a rolled-up sheet, a twisted sheet, or a braided sheet. One shape is a planar material (square, rectangle, oval, or other) that is rolled-up. The rolling can contribute mechanical properties such as uncurling to force the material against a track.

For instance, an embodiment is a rod of lyophilized hydrogel with a circular or oval cross-section, which after coating or dusting with a reactive hydrogel coating, may be inserted into vascular tracks for closure. A solid rod does not need to uncurl, resulting in improved application consistency. Alternatively, lyophilized hydrogels can be made in a planar shape, rolled, and placed within a sheath and introduced percutaneously. The coating may be on only the exterior or a portion of the rolled-up shape or the planar shape may receive a continuous or discontinuous coating before rolling. Upon deployment, the hydrogel coating dissolves and forms a reactive thin film that can help adhere the lyophilized hydrogels over and around the access site.

The adherence, strength and swelling of the lyophilized hydrogel biomaterial substrate can be controlled by the amount, pattern and type of the hydrogel coating. Adhesives used in vascular access tracks have a significant mechanical advantage relative to other bioadhesive uses. For example, sealants used to seal blood vessel anastomoses in open surgical procedures depend heavily on both tissue adherence to the adventitia adjacent to the anastomosis, and on the cohesive strength of the adhesive itself. This cohesive strength of such materials is an important factor, even though the adhesive may be only 1-2 mm thick. One mechanical advantage is that the walls of the track provide a large surface area for adherence, and the resulting plug can be provided that has a high cohesive strength due to its greater thickness. Thus, this increased surface for adherence and longer path length allow these vascular access closure adhesives to function more as adherent plugs than as patches, allowing them to withstand higher pressures.

Figure 7:
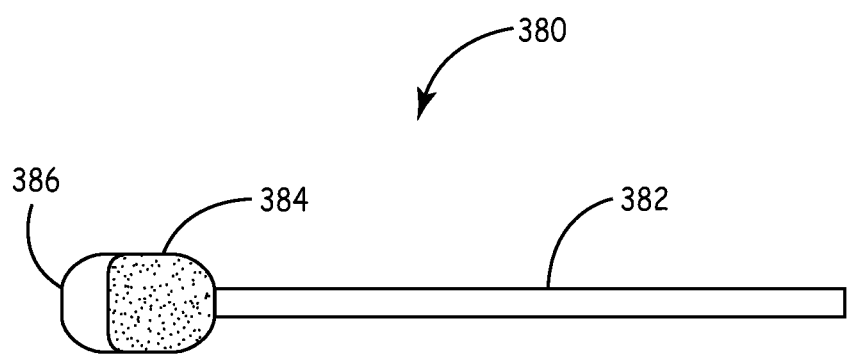
FIG. 7 depicts an embodiment of a hand-held swab applicator.

Another use of a coated material is a swab applicator for sealing a track. Coatings of precursors may be located on biomaterials delivered into a puncture tract or placed on applicators to wipe them onto the tissue tract lumen. One embodiment for preparing the precursors is a lyophilization from a frozen liquid. FIG. 7 depicts swab applicator 380 with rod 382, swab 384, and coating 386. The coating may be a coating as described herein, e.g., a coating comprising one or more precursors in a dry state that form a matrix upon exposure to a physiological fluid. Moreover, the coating may be supplemented with coagulation factors, e.g., salts, calcium salts, metal salts, thrombin, collagen, fibrin(ogen), or blood clotting factors that participate in the intrinsic or extrinsic blood clotting cascade. The swab 384 may be provided with a diameter suited to percutaneous track passage, with a maximum gauge of about 1 to about 6 mm; artisans will immediately appreciate that all the ranges and values within the explicitly stated ranges are contemplated, e.g., from about 1 to about 3, from about 1 to about 4, or from about 2 to about 3 mm, or less than about 5 mm or less than about 3 mm. The maximum width, also referred to somewhat loosely as a maximum diameter, is the maximum length that a track is to be distended. The term "gauge" refers to the smallest diameter circular opening that a device can pass through. The same ranges and/or values may be expressed in terms of maximum circumference by using the formula circumference=$2\pi R$, with R being from about 1 to about 3 mm. As depicted, the coating partially covers the swab but may alternatively cover all of it. Moreover, the shape of the swab may be tear-shaped, round, ellipsoidal, or other shapes. The rod may be plastic, metal, wood, or other material with a stiffness and strength suited to the swabbing use.

Figure 8A:
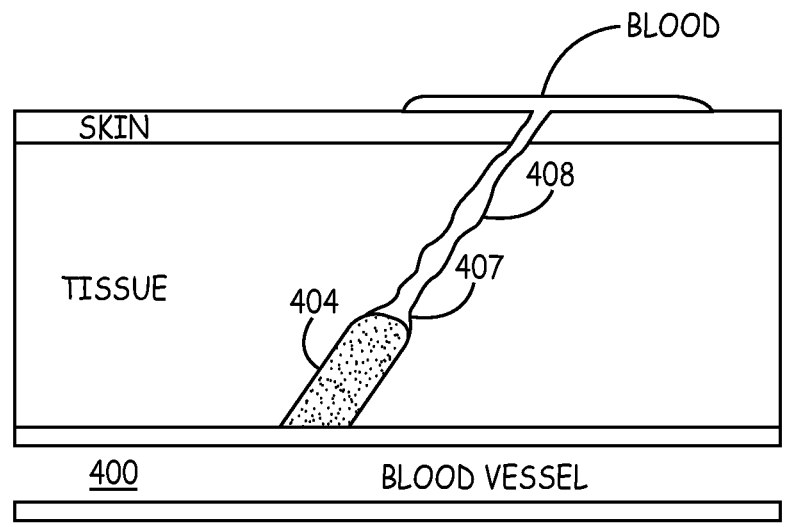
FIG. 8A depicts a plug deployed in a vascular access site.
Figure 8B:
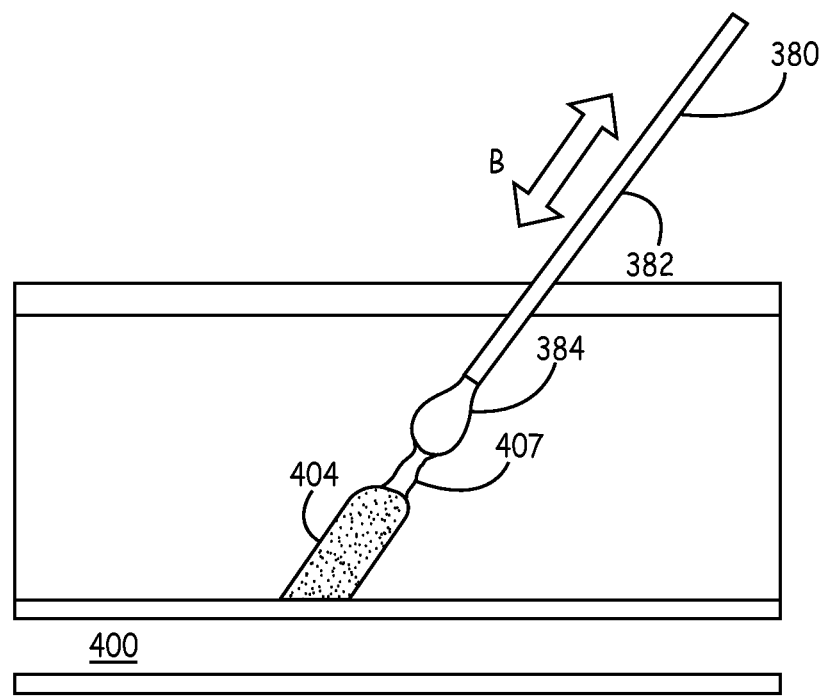
FIG. 8B depicts a process of using the embodiment of FIG. 7 in the site of FIG. 8A.
Figure 8C:
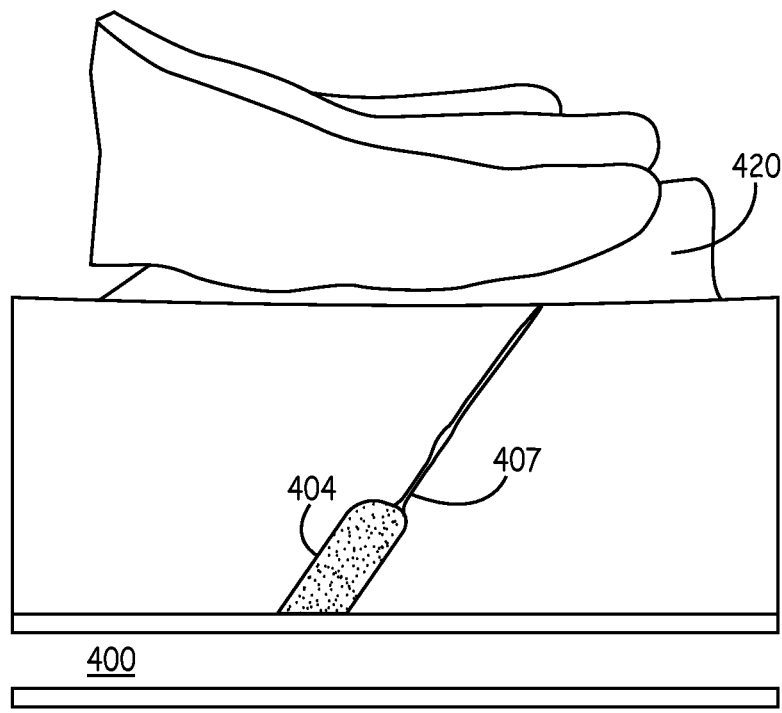
FIG. 8C depicts a further process of using the embodiment of FIG. 7 in the site of FIG. 8A.
Figure 8D:
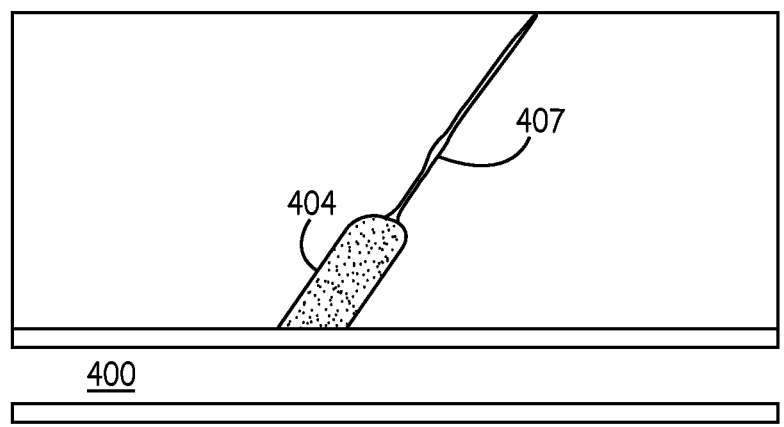
FIG. 8D depicts an outcome of a process of FIG. 8C.

The swab may be used in any track, be it from biopsy of a tissue or organ or a result of percutaneous vascular access. The swab may be used by itself, in combination with manual tamponade, or in combination with a plug. The latter use is depicted in FIG. 8. At FIG. 8A, a blood vessel 400 with a puncture 402 has been plugged with a plug 404 placed in track 407. Blood 408 has seeped from the walls of track 406 into the track and onto the skin. As shown in FIG. 8B, a user moves swab applicator 380 through track 407 to brush coating 386 onto the walls of the track, with movement as at arrow B. As shown in FIG. 8C, mechanical tamponade 420, e.g., manual pressure or pressure mediated by a device or adhesive, compresses track 407, with coating 386 precursors reacting to form a matrix that contributes to closure. After a predetermined time (e.g., 30 seconds to 10 minutes; artisans will immediately appreciate that all the ranges and values within the explicitly stated ranges are contemplated), the pressure is removed, with track seepage being stopped, as at FIG. 8D.

Bleeding from the vessel track could thus be controlled with the use of a precursor coated applicator that is introduced into the track and moved in and out, or spun around, allowing the coating to dissolve and coat the track tissues. A coated enlargement on the distal end could be used to both clear blood from the track and to ensure intimate contact between the dissolved precursors and the tissue as the rod is advanced in and out. A brief external compression applied when the swab is pulled from the track would allow the track to be glued closed as the hydrogel polymerizes. Additionally, this compression may remove precursors at the skin level, eliminating the possibility of having a continuous length of gel from the skin to the vascular closure device. With the track glued shut, bleeding from the track tissue would be controlled, and would not be allowed to reach the skin surface. A degradable biomaterial could absorb within hours or 1-30 days of application (artisans will immediately appreciate that all the ranges and values within the explicitly stated ranges are contemplated, e.g, 1 to 5 days), as longer persistence would not be required.

FIG. 9 depicts device 450 for applying a mechanical pressure to skin. Sheet 452 with coating 454 is applied to a patient's skin, with base 456 being secured thereupon with strap 458 having an adjustable feature, as in holes 460 that receive knob 462. Alternatively, buckles, snaps, or other adjustment means may be used. After a predetermined time, e.g., 10 seconds to 10 minutes, the backing is removed. The sheet may be biodegradable or removable. Release agents may be placed between the sheet and coating to facilitate removal.

Coatings and materials as set forth herein may be used. The coating provides adherence to a tissue. For instance, a puncture track on a wrist or for brachial access, or other locations may have a short track that is not well suited to receiving an implant into the track. For this or other applications, the backing material receives a coating of precursors that react with fluid from the tissue to form an adhesive hydrogel. The backing is left on until the healing process is complete or may be removed after adhesion is established. A biomaterial may be placed between the backing and the coating to provide further structure. Release agents may be included as needed to assist removal of the backing. The backing material and/or biomaterial may have, e.g., a planar shape, for instance, a rectangular, square, circular, or oval sheet. The base for applying a compressive force is optional. The base spreads a compressive force through the base and backing to compress an adhesive coating against a tissue surface.

Alternatively, a powdered mix may be applied into the track or tissue site before introduction of a biomaterial. For instance, a powder may be drawn up within a sheath below a position occupied by a lyophilized hydrogel biomaterial within the sheath. When the lyophilized hydrogel is ejected into the access site, the dry precursors are also ejected and begin dissolving and reacting. Alternately, a biomaterial may be dusted with such powders.

FIG. 10 depicts an embodiment that exemplifies introducing precursors into a track in combination with a plug, and optionally in the same applicator as the plug. Applicator 500 has sheath 502 and push rod 504. Sheath 502 has handles 506 and distal tip 508. Push rod 504 has handles 510 and optionally removable stop 512. A permanent stop may alternatively be used, for example, an enlarged diameter portion of the push rod that provides resistance without preventing continued movement. Sheath 502, FIG. 10B, is preloaded with plug 516 and precursor or precursors 518. A non-reactive agent 520, e.g., a release agent, may further be preloaded at the distal end portion 522. The non-reactive agent 520 provides for absorption or repulsion of fluids prior to release of precursors 518. The non-reactive agent does not form a matrix material but is optionally a coagulation enhancing material as already described. Distal tip 508 and at least an accompanying portion of sheath 502 is sized for track entry (e.g., small, or medium, or large bore), and is introduced into track 524.

Figure 10A:
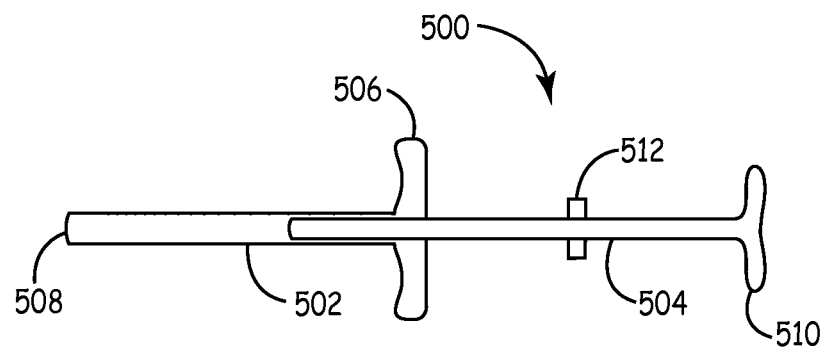
FIG. 10A depicts an applicator.
Figure 10B:
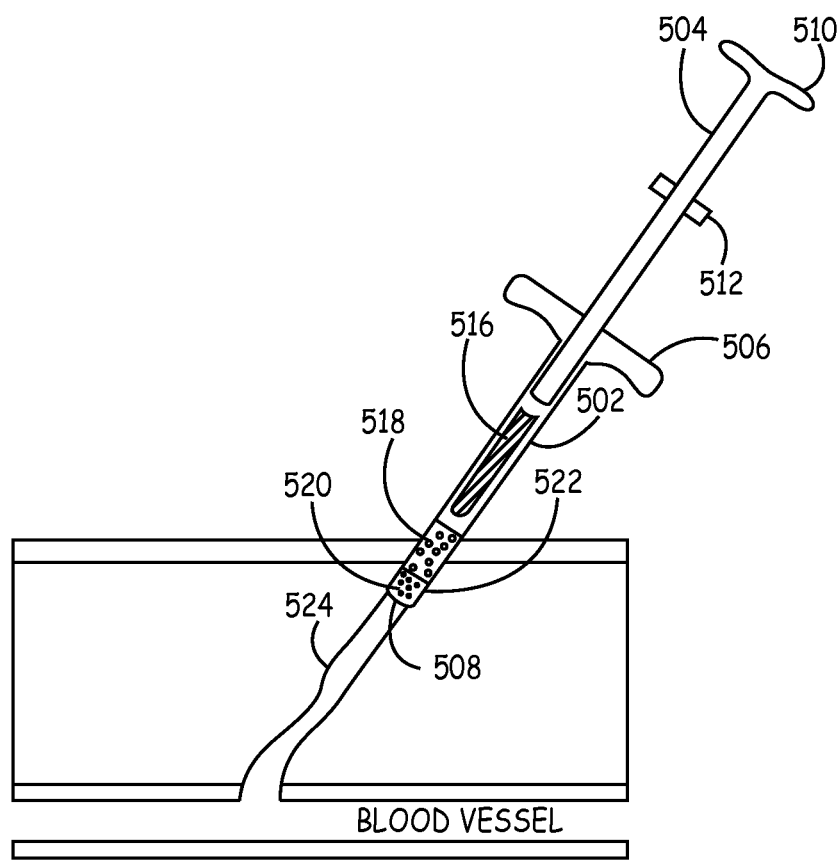
FIG. 10B depicts the applicator of FIG. 10A in use at a vascular access site for delivery of a precursor and a plug.
Figure 10C:
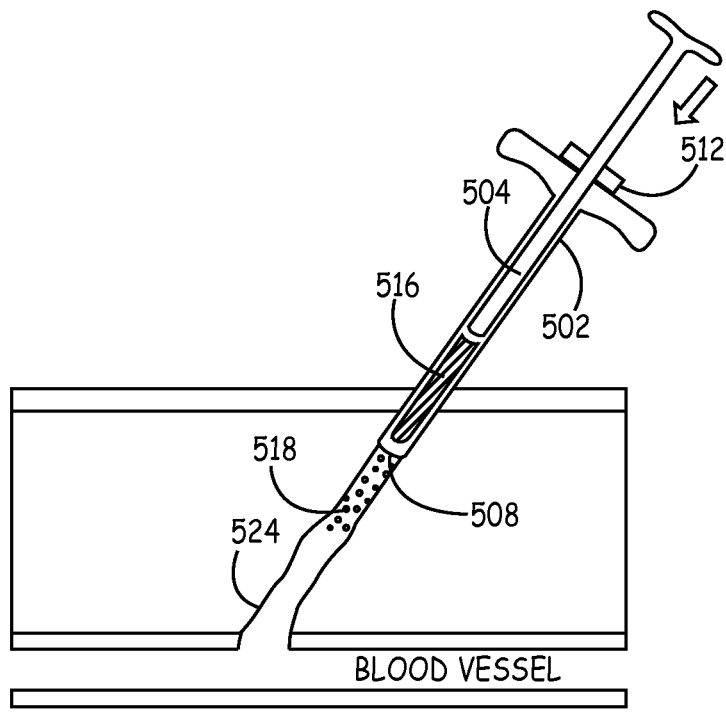
FIG. 10C depicts the applicator of FIG. 10B in a process of delivering the precursor.
Figure 10D:
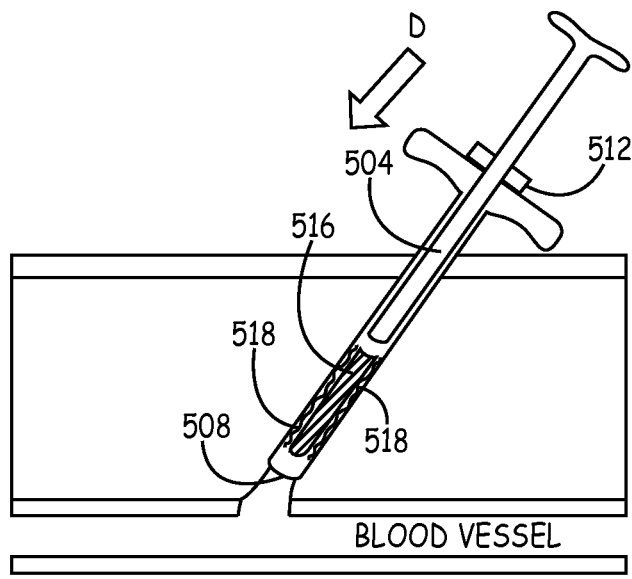
FIG. 10D depicts the applicator of FIG. 10C in a process of delivering the precursor.
Figure 10E:
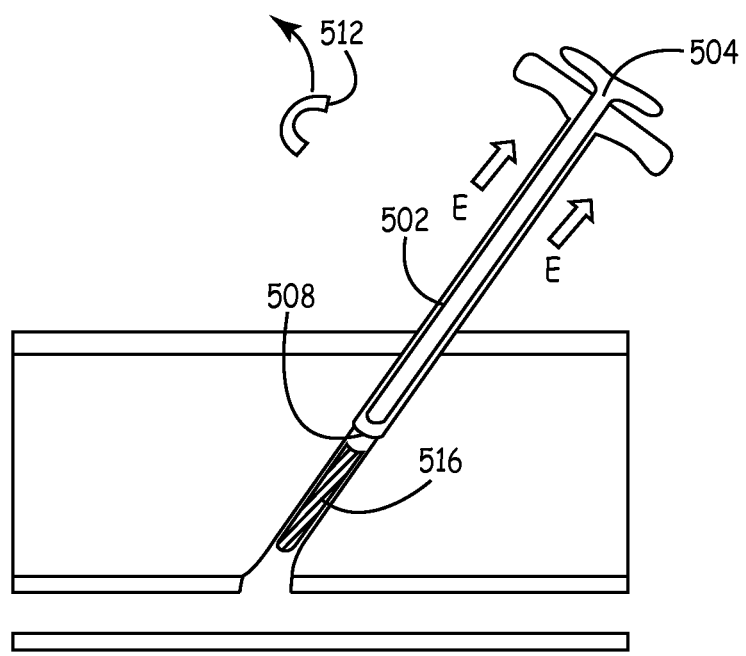
FIG. 10E depicts the applicator of FIG. 10B in a process of delivering the plug.

At FIG. 10C, the push rod 504 is pushed until stopped by stop 512, expelling precursors 518 and any accompanying materials. As depicted, the precursors are expelled in the proximal half of the track, but may be expelled at other positions, e.g., the proximal (skin side) opening of the track, the track midpoint, or the distal half or distal tip of the track. As shown in FIG. 10C, sheath 502 is further pushed downwardly, arrow D, and precursors 518 are distributed on the walls of the track. Plug 516 is expelled, FIG. 10E, with removable stop having been removed, and sheath 502 being drawn upwardly as at arrows E, and applicator 500 is removed. Various tamponading or swabbing steps may further optionally be employed.

Various embodiments have been described herein and may be directed to sealing medium or large bore punctures although the same embodiments could also be used to seal smaller punctures if sized accordingly. One of the motifs is to use a coating of matrix precursors on, or with, an acceptably shaped article made from a biomaterial that can be introduced into the track. The dry precursors, which are present either as a coating, or co-located in the percutaneous closure system, dissolve when exposed to liquids at the site needing closure, and polymerize over a period of time, thus securing with adherence the plug to the site needing closure and effecting such closure. The entire materials and mechanism can be prepared with systems and devices compatible with percutaneous use. Various precursors and biomaterials are described herein for the same. Another motif is that a biomaterial for the large (or other) bore puncture is coated on a proximal end. An applicator is placed in the track and the biomaterial is at least partially forced into the track to reveal at least part of a coating on the material. The material is optionally compressed therein by a member of the applicator, e.g., a push-rod. The proximal end adheres to the tissue track. The biomaterial may be expelled from an applicator all at once or partially exposed in stages, e.g., so that the proximal end with the adhesive is not exposed until immediately prior to adhesion.

Other embodiments provide for a coating at the distal end of a biomaterial placed into a track. An applicator is introduced into the track and manipulated to place at least a part of the distal portion into the track, e.g., by a push rod that forces the material out of a sheath containing the material. The revealed portion's coating adheres to the tissue and the sheath is further withdrawn. The material is optionally compressed. The adhesive coating will thus secure the hydrogel at the site of the closure to better seal such larger (or other sized) punctures and/or tracks.

In the case of arteriotomy, a useful area for sealing is near an arteriotomy in a distal portion of the track. The desiccation of track blood by water uptake into the coating and optionally the underlying biomaterial would tend to leave high viscosity layer of blood between the biomaterial/coating and the tissue to further contribute to adhesivity.

In addition to biomaterials and/or coatings being used to seal a puncture or other iatropic site, lyophilized hydrogels with or without coatings can be used in the same track for needle track (or other puncture device track) hemostasis, and to act as a space filler supporting the biomaterials against vascular pressure. In one embodiment, a first biomaterial is placed in a distal portion of the track and a second device (same or different biomaterial) is placed in a proximal portion of the track.

Alternatively or additionally, a skin closure (suture, clip, glue, tape) may be placed at the skin to help to hold the biomaterials in place, while also reducing the potential of blood pressure pushing the biomaterials from the vascular track. Such closures may generally be used, e.g., for one or more biomaterials placed into a track, with the biomaterial(s) being coated or uncoated.

For instance, in addition to lyophilized hydrogel with a coating being used to seal the puncture or other iatropic site, lyophilized hydrogels without coating can be used in the same track for needle track hemostasis, and to act as a space filler supporting the sealed lyophilized hydrogels against vascular pressure. The skin closure (suture, clip, glue, tape) may be used help to hold the lyophilized hydrogel biomaterial in place, while also reducing the potential of blood pressure pushing the lyophilized hydrogel(s) from the vascular track.

Some embodiments do not fill the track but instead are placed topically over the track, e.g., as in a brachial access site. The backing with coating and/or biomaterial embodiments described herein may be used for this application. Some of the coating and/or biomaterial may be forced into a proximal portion of the track, with the same being biodegradable and providing a sealing role.

The application of coatings consisting of dry PEG precursors to sheets of backing materials has previously been disclosed. However, the use of these coatings were envisioned for open surgical situations, and not for interventional purposes. Different design requirements exist between these coated open surgical and coated interventional devices so that different materials must be chosen and combined. For example, in open surgery, it is desirable that the backing materials be non-swelling, so as to not lose strength and not distort underlying tissues. In contrast, swelling or expanding backing materials may be advantageous in interventional applications.

In contrast to other adhesive systems that require using a solution of materials, the coating-based approaches described herein could be processed to provide better shelf life stability by storage in an oxygen and moisture free environment (e.g., foil pouch). Also, placing a coated device would generally be easier than placing a device that further requires combination with an adhesive at the same time, i.e., the coatings are easier to use. As no reconstitution in solvent is required, these devices should be immediately ready to use once removed from their packaging.

Different coating strategies can be used for different applications. Continuous coating on one side can result in adherence to tissue, while minimizing or eliminating adherence from the other. Coating on both sides (top) can result in uniform adherence on both surfaces, with less substrate absorption and swelling. In contrast, coating with dots or lines on one or both sides (middle and bottom), or on the edges, could allow for directional tissue adherence while still allowing for fluid absorption and substrate swelling.

Various embodiments with various features have been disclosed by way of example to illustrate the invention. The features of the various embodiments may be mixed-and-matched to provide further combinations and subcombinations as guided by the need to make functional embodiments. The headings and subheadings are merely for convenient reference and are not limitations as to disclosure.

An apparatus for treatment of an iatropic track and blood vessel puncture comprising an applicator and a plug, with the applicator comprising a distal sheath portion sized for placement in the track and having a distal opening and a lumen, and a pusher received by the lumen for pushing the plug out of the lumen through the sheath distal opening, with the plug being sized for placement in the track and comprising a coated portion with a substantially dry coating, wherein the coating comprises at least one precursor that dissolves in physiological fluid after placement in the track and undergoes a covalent bonding reaction to form a matrix material that adheres the plug to the track and/or blood vessel, and an uncoated portion that exposes a porous portion of the plug to blood in the track, with the porous portion at least partially dehydrating the blood in the track.

A method for treatment of an iatropic track and blood vessel puncture comprising percutaneously introducing a porous plug into the track through an applicator having a lumen terminating in a distal opening, the plug comprising a dry coating on a distal portion of the plug and being free of the coating on a proximal portion of the plug, wherein the coating comprises at least a first precursor that dissolves in physiological fluid after placement in the track and undergoes a covalent bonding reaction to form a matrix material that adheres the plug to tissue of the track and/or blood vessel, with the coating promoting adhesion at or near the puncture and the uncoated portion of the plug at least partially dehydrating blood in the track to reduce flow of blood from the lumen of the track into the track.

An apparatus for treatment of an iatropic track and blood vessel puncture comprising an applicator, a plug, and at least a first precursor, with the applicator comprising a distal portion sized for placement in the track and having a distal opening and a lumen, and a pusher at least partially received in the lumen for pushing the plug out of the lumen through the distal opening, with the plug being sized for placement in the track and disposed within the lumen, and with the precursor being disposed in the lumen at a position distal to the plug for release into the track prior to expulsion of the plug from the lumen, wherein the precursor dissolves in physiological fluid after placement in the track and forms a matrix material.

A method for treatment of an iatropic track and blood vessel puncture comprising placing a distal portion of an applicator into the track, expelling a reactive precursor from the applicator into at least a portion of the track, and subsequently expelling a plug into the track, wherein the precursor forms a matrix material adhesive to the track lumen and substantially stops flow of blood from walls of the track into the track lumen.

An apparatus for treatment of an iatropic track and blood vessel puncture comprising an applicator, a plug, and at least a first precursor, with the applicator comprising a distal portion sized for placement in the track and having a distal opening and a lumen, and a pusher at least partially received in the lumen for pushing the plug out of the lumen through the distal opening, with the plug being sized for placement in the track and disposed within the lumen, and with the precursor being disposed in the lumen at a position distal to the plug for release into the track prior to expulsion of the plug from the lumen, wherein the precursor dissolves in physiological fluid after placement in the track and forms a matrix material.

A method for treatment of an iatropic track and blood vessel puncture comprising placing a distal portion of an applicator into the track, expelling a reactive precursor from the applicator into at least a portion of the track, and subsequently expelling a plug into the track, wherein the precursor forms a matrix material adhesive to the track lumen and substantially stops flow of blood from walls of the track into the track lumen.

A handheld applicator comprising a proximal portion graspable by a user and a distal portion comprising a swab coated with at least a first precursor that, in the presence of a physiological fluid, reacts to form a matrix, with the coated swab having a maximum gauge of no more than about 5 mm.

A method of preventing blood flow in a tissue track comprising wiping the track walls with a swab coated with a matrix precursor that dissolves in physiological fluid in the track and forms a matrix on walls of the track for stopping the blood flow, with the coated swab having a maximum gauge of no more than about 5 mm.

An applicator comprising a sheet disposed on a radially expandable member, with the sheet being a biodegradable biomaterial coated with one or more precursors that form a tissue adherent matrix upon exposure to a physiological fluid to adhere the sheet to the tissue, with the radially expandable member being operable to radially expand the sheet and thereafter be completely separated from the sheet, wherein the sheet further comprises an opening coaxial with a central axial bore of the applicator, with the applicator having a maximum gauge of no more than about 1 or 3 or 5 mm.

A method of sealing a percutaneous vascular access site comprising passing an occlusion device through a track that leads to the site and occluding a puncture in a blood vessel at the site, with the occlusion device being connected to an elongate member that passes through the track, passing an applicator over the elongate member, with the applicator comprising a sheet disposed on a radially expandable member, with the sheet being a biodegradable biomaterial coated with one or more precursors that form a tissue adherent matrix upon exposure to a physiological fluid, radially expanding the radially expandable member to thereby radially expand the sheet and forcing the coating against a tissue, with the coating dissolving to form a matrix adherent to the tissue, separating the applicator from the sheet, and withdrawing the applicator, elongate member, and occlusion device from the site.

The method, apparatus, or system as in the foregoing, provided as a kit. The kit may be provided in a single sterile package. Precursors and make-up water and/or buffers may be included.

EXAMPLE 1

Melted 4a20kSG (four-armed 20,000 MW succinimidyl glutarate-terminated polyethylene glycol polymer) and 8a20k amine (eight-armed 20,000 MW amine-terminated polyethylene glycol polymer) (2:1 ratio) were combined and brought to a temperature of 50° C. The experimenters briefly wiped both sides of a lyophilized PEG-based hydrogel (sheet rolled end-to-end) onto a hot plate containing the melted polymer. This was tried with and without borate buffer coating, to raise the reaction pH and accelerate polymerization, on the lyophilized hydrogel prior to polymer application.

Once cooled, the samples were hydrated with physiological saline and squeezed between two fingers. The resulting adherence to the fingers was strong; in fact, when pulled apart, the samples failed cohesively, and not at the adhesive-skin interface.

EXAMPLE 2

Figure 11:
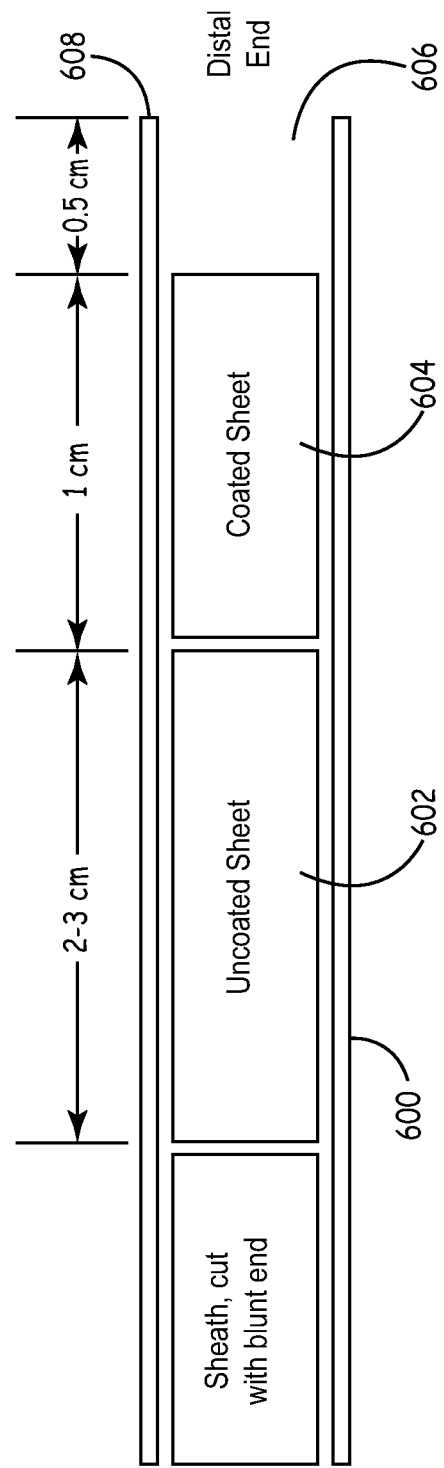
FIG. 11 is an embodiment of a plug system as used in Example 2.

A lyophilized PEG-based hydrogel as used in a MYNX system was obtained in a flat unrolled state. The sheet was rolled and placed in the lumen of a 11 Fr sheath that was about 6 inches long. A second sheet of the same material was placed on a melt of PEG precursors at a temperature of about 75° C. The melt was a 1:1 ratio of methylene blue and 4a10CM:8a20k amine (a 4-armed 10 kDa polyethylene glycol precursor terminated with carboxymethyl hydroxybutyric acid precursor and a second precursor that is an 8 armed 20 kDa multifunctional PEG terminated with amines). The sheet was removed and allowed to cool, at which point it was coated on one side and was not tacky. The sheet would tend to curl or shrink if exposed to too high of a temperature. The coating tended to form cracks when thick but was free of cracks in thinner coatings. The coated sheet was rolled and placed into the sheath. FIG. 11 depicts this arrangement. Sheath 600 contains uncoated rolled sheet 602 and adjacent rolled and coated sheet 604, with a small gap 606 at the distal end 608 of the sheath, which was open.

A test apparatus was constructed with a three-way valve that connected a digital pressure gauge, a syringe of about 10 ml volume having a buffer solution, and a 1-ml plastic syringe in a vertical, upright position with the plunger removed. The valve was turned to a first position so that the 1-ml syringe was isolated. The lower portion of the 1-ml syringe was filled with physiological buffer solution. The sheath was introduced into the 1-ml syringe and a pusher rod was used to push the plugs out of the sheath and into the bottom of the syringe. The sheath and pusher rod were used to force the sheets down and were held in place for a about a minute. The precursor reacted in the buffer and formed an adhesive matrix that adhered both sheets to the bottom of the syringe. The sheath and the pusher rod were removed. The three-way valve was moved to a position that allowed communication between the 1-ml syringe, the 10-ml syringe, and the pressure gauge were in communication with each other. The 10-ml syringe was used to force fluid through the valve while the pressure gauge was observed. Pressures in excess of 1000 Torr were observed with no leaking or movement of the sheets. The test was repeated several times with different sheets. The precursors reacted to form both rolled sheets into a single cohesive mass. The most distal portion of the distal sheet assumed the shape of the syringe distal end, a male Luer-Lock shape, showing compressibility and moldability.

As is evident, other embodiments of this exemplary system may be made using the precursors and materials and devices set forth herein.

It is claimed:

1. An apparatus for treatment of a track and blood vessel large bore puncture comprising:
    an applicator, a plug comprising a proximal and a distal end preloaded in the applicator, and first and second reactive precursors preloaded in the applicator,
    with the applicator comprising a distal portion sized for placement in the track of the large bore puncture and having a distal opening and a lumen, and a pusher at least partially received in the lumen for pushing the plug out of the lumen through the distal opening,
    with the plug being sized for placement in the track of the large bore puncture and disposed within the lumen, and
    with the precursors disposed in the lumen at a position distal to the distal end of the plug for release into the track of the large bore puncture prior to expulsion of the plug from the lumen,
    wherein the precursors are a powder in a dry state and react with physiological fluid after placement in the track to dissolve and form a matrix material that secures the plug within the puncture.

2. The apparatus of claim 1 wherein the first reactive precursor comprises electrophilic functional groups and the second reactive precursor comprises nucleophilic functional groups, wherein both of the precursors are polymers.

3. The apparatus of claim 1 wherein the plug comprises a rod, a tube, a rolled-up sheet, a twisted sheet, or a braided sheet.

4. The apparatus of claim 1 wherein the precursors dissolve in physiological fluid after placement in the track and undergo a covalent bonding reaction to form a matrix material that adheres to the plug and the track.

5. The apparatus of claim 1 comprising a plurality of the reactive precursors, wherein the precursors dissolve in physiological fluid after placement in the track and undergo a covalent bonding reaction to form a matrix material that adheres to the plug and the track.

6. The apparatus of claim 1 wherein the plug comprises a porous hydrogel.

7. The apparatus of claim 1 wherein the plug comprises a lyophilized hydrogel biomaterial.

8. The apparatus of claim 1 further comprising a buffer to increase a reaction rate of the precursors when exposed to fluid within the track.

9. The apparatus of claim 1 wherein the applicator comprises a sheath.

10. A method for treatment of a track and blood vessel puncture comprising:
    placing a distal portion of an applicator into the track, the applicator preloaded with a plug having proximal and distal ends and first and second reactive precursors distally beyond the distal end of the plug, wherein the precursors are a powder in a dry state and react with physiological fluid to dissolve the precursors;
    expelling the precursors from the applicator into at least a portion of the track, and subsequently expelling the distal end of the plug into the track, wherein the precursors react and form a matrix material adhesive to the track and the treatment substantially stops flow of blood into the track;
    wherein the puncture is a large bore puncture.

11. The method of claim 10 wherein the plug is expelled into the track and pushed through at least a portion of the track that received the precursors.

12. The method of claim 10 wherein the precursors are expelled into the track and a distal portion of the applicator is passed through at least a portion of the track that received the reactive precursors, and the plug is expelled into the track.

13. The method of claim 10 wherein the first precursor comprises electrophilic functional groups and the second precursor comprises nucleophilic functional groups, wherein both of the precursors are polymers.

14. The method of claim 10 wherein the plug comprises a rod, a tube, a rolled-up sheet, a twisted sheet, or a braided sheet.

15. The method of claim 10 wherein the precursors dissolve in physiological fluid after placement in the track and undergo a covalent bonding reaction to form a matrix material that secures the plug within the track.

16. The method of claim 10 comprising a plurality of the reactive precursors, wherein the precursors dissolve in physiological fluid after placement in the track and undergo a covalent bonding reaction to form a matrix material that adheres to the plug and the track.

17. The method of claim 10 comprising melting the precursors, with the melted precursor material being located distal to the plug in the applicator.

18. The method of claim 10 wherein the plug comprises a porous hydrogel.

19. The method of claim 10 wherein the plug comprises a lyophilized hydrogel biomaterial.

20. The method of claim 10 further comprising a buffer to increase a reaction rate of the precursors when exposed to fluid within the track.

21. The method of claim 10 wherein the applicator comprises a sheath.

22. The method of claim 21 further comprising passing the sheath over an introducer wire.

23. The method of claim 10, further comprising placing an elongate member including an expandable member into the track and expanding the expandable member within a body lumen adjacent the track, and wherein the precursors and plug are expelled from the applicator at a position around the elongate member and proximal the expanded expandable member.

24. The method of claim 23, further comprising removing the expandable member and applicator from the track through the plug.

25. A method for treatment of a track and blood vessel puncture, comprising:
    providing an applicator with a proximal end portion and a distal end portion preloaded with a plug having a proximal and a distal end and first and second reactive precursors distally beyond the distal end of the plug adjacent a distal end portion of the applicator, wherein the precursors are a powder in a dry state and react with physiological fluid to dissolve the precursors;
    positioning the distal end portion of the applicator near an arteriotomy in a distal portion of the track; and
    sequentially expelling the precursors and the plug from the distal end portion of the applicator into the track, wherein the precursors react and form a matrix material that secures the plug within the track relative to the arteriotomy,
    wherein the puncture is a large bore puncture.

26. The method of claim 25, wherein the plug is a lyophilized hydrogel biomaterial.

27. The method of claim 26, wherein the first precursor comprises electrophilic functional groups and the second precursor comprises nucleophilic functional groups, wherein both of the precursors are polymers.

28. The method of claim 25, further comprising introducing additional sealing material into all or a portion of the track.

* * * * *